(12) United States Patent
Pravata

(10) Patent No.: US 8,835,528 B2
(45) Date of Patent: Sep. 16, 2014

(54) ADHESIVE COMPOSITION

(75) Inventor: Laurent Pravata, Beaufays (BE)

(73) Assignee: Synolyne Pharma, Herstal (BE)

( * ) Notice: Subject to any disclaimer, the term of this patent is extended or adjusted under 35 U.S.C. 154(b) by 0 days.

(21) Appl. No.: 13/320,004

(22) PCT Filed: May 12, 2010

(86) PCT No.: PCT/EP2010/056574
§ 371 (c)(1),
(2), (4) Date: Nov. 10, 2011

(87) PCT Pub. No.: WO2010/142507
PCT Pub. Date: Dec. 16, 2010

(65) Prior Publication Data
US 2012/0053261 A1  Mar. 1, 2012

(30) Foreign Application Priority Data

May 13, 2009 (EP) .................................. 09160133

(51) Int. Cl.
| | | |
|---|---|---|
| *C08L 5/08* | (2006.01) | |
| *A61L 15/58* | (2006.01) | |
| *C08B 37/08* | (2006.01) | |
| *A61L 24/08* | (2006.01) | |
| *C09J 105/08* | (2006.01) | |

(52) U.S. Cl.
CPC ............... *C08B 37/003* (2013.01); *A61L 24/08* (2013.01); *C09J 105/08* (2013.01); *A61L 15/58* (2013.01)
USPC ............ 523/118; 523/105; 523/113; 523/114

(58) Field of Classification Search
None
See application file for complete search history.

(56) References Cited

U.S. PATENT DOCUMENTS

| 4,619,995 | A  | * | 10/1986 | Hayes .............................. 536/20 |
| 5,578,661 | A  | * | 11/1996 | Fox et al. .......................... 524/27 |
| 6,379,702 | B1 | * | 4/2002  | Lorenz et al. ................. 424/488 |
| 7,901,707 | B2 | * | 3/2011  | Allen et al. ................... 424/443 |
| 8,158,720 | B2 | * | 4/2012  | Reddy et al. ................. 525/54.2 |
| 2002/0111576 | A1 | * | 8/2002 | Greene et al. ................... 602/42 |
| 2003/0225356 | A1 | * | 12/2003 | Kulichikhin et al. ........... 602/54 |
| 2005/0112182 | A1 | * | 5/2005 | Minami et al. ................ 424/448 |
| 2006/0029578 | A1 | * | 2/2006 | Hoemann et al. ............ 424/93.7 |
| 2006/0293446 | A1 | * | 12/2006 | Reddy et al. ................ 525/54.2 |

FOREIGN PATENT DOCUMENTS

WO  WO 2008061999 A1 * 5/2008

OTHER PUBLICATIONS

Zhao, et al. "Synthesis of Bioadhesive Hydrogels from Chitin Derivatives," *International Journal of Adhesion & Adhesives*, vol. 21, pp. 227-232, Jan. 1, 2001.
International Search Report dated Jan. 12, 2011 issued to international application No. PCT/EP2010/056574.

\* cited by examiner

*Primary Examiner* — James J Seidleck
*Assistant Examiner* — Peter A Salamon
(74) *Attorney, Agent, or Firm* — Knobbe, Martens, Olson & Bear LLP

(57) ABSTRACT

The invention relates to a new biocompatible, biodegradable removable and repositionable adhesive composition, its preparation method and various uses thereof, including its use as surgical aid. The invention also discloses a matrix comprising such composition, such as e.g. a solid support covered, impregnated or saturated by said adhesive composition. Adhesive compositions according to the invention comprise at least one chitin and/or chitosan containing material. In a particular embodiment said adhesive composition further comprises at least one adhesive-enhancing agent whereby said agent is provided in a granular form, and preferably is a chitin and/or chitosan containing material as defined herein. The present adhesive composition and matrix comprising such composition can be used as gluing composition, in particular in wound-healing and/or surgical applications.

18 Claims, 6 Drawing Sheets

ADHESIVE COMPOSITION

CROSS-REFERENCE TO RELATED APPLICATIONS

This application is the U.S. National Phase under 35 U.S.C. §371 of International Application PCT/EP2010/056574, filed May 12, 2010, which claims priority to EP 09160133.6, filed May 13, 2009.

TECHNICAL FIELD

The present invention relates to the field of adhesive compositions and uses thereof, especially in the medical and surgical field. More in particular, the invention relates to an adhesive, removable and repositionable composition comprising a chitin containing material and/or a chitosan containing material and to various uses thereof.

BACKGROUND

In recent years there has been increasing interest in improving adhesives and sealants in the field of surgical aids for improving the efficiency of classical sutures or for replacing them partially or totally and thus suppressing the need of using yarns or staples or other invasive suture and tissue repair materials.

Improved adhesives and sealants are also needed for fixing materials such as membranes, meshes, sheets, bandages, prostheses etc. . . onto living soft or hard tissues including e.g. muscles, skin, nerves, tendons, ligaments, blood vessels, bones, cartilages, nails, hair, teeth etc. . . that partially or totally suppress the need for using yarns, staples, screws, pins or other fixing devices that can damage or provoke additional injury to tissues or nerves and provoke pain.

Also improved adhesives and sealants that enable perfect closure when requested and avoid leakage of fluids are needed. The use of adhesive and sealants is also preferred for avoiding excessive deformation of the tissue to be repaired.

Several compositions that are used as adhesive or sealant for tissue adhesion or for fixing materials or devices onto tissues are currently commercially available. Nevertheless, these compositions show relevant drawbacks.

For instance, cyanoacrylate-based products are known for a very long time as efficient surgical glues. Such compositions are highly adhesive, in very short periods of time. Cyanoacrylate adhesive compositions harden very quickly which is a hurdle for its use in the field of tissue repair, or for fixing solid supports onto living material. As a matter of fact, such high strength and fast-hardening glues exclude the removal and further repositioning of the material to be stuck. Moreover neither the biocompatibility nor the non-toxicity have been demonstrated and it has been suspected that the exothermic reaction during the hardening process provokes the release of toxic degradation compounds.

Fibrin sealant products which are based on the polymerization of fibrinogen and thrombin in the presence of growth factor XIII and fibronectin lead to the formation of a fibrin clot which enables sticking.

Proteins, such as collagen and albumin, cross-linked with aldehyde are also already used and commercialized (GRF (Gelatine Resorcine Formaldehyde) glue or French glue). Concern regarding the toxicity of the cross-linking agents used in this technology has frequently been raised. Moreover, the mammalian origin of both collagen and albumin constitutes a major concern for approval onto the market due to pronounced risks of allergenic, immunogenetic or infectious related diseases.

Natural polyphenolic adhesive proteins secreted by organisms such as mussels (*Mytilus edulis*) as well as their synthetic analogues are capable of adhering to a variety of surfaces under water when cross-linked and thus have also raised interest recently. However the cost-effectiveness and in some cases the use of toxic cross-linkers may compromise such approaches.

Polyethylene glycol (PEG) polymers used for tissue adhesion are also on the market. They need to be mixed and photopolymerized for activating the adhesion (FocalSeal-L, Genzyme Biosurgery, Inc.) which makes them difficult to use. Similar products have been developed that do not require photopolymerization and rely on mixing and reaction of N-hydroxysuccinyl PEG and thiolated PEG powders with acidic aqueous solution (CoSeal®, Angiotech Pharmaceuticals, Inc.). However the preparation is long and the injection of local acid and basic solutions present safety concerns. DuraSeal® (Confluent Surgical, Inc.) is another example of two-part self-curing PEG hydrogel products (PEG ester solution and a trilysine amine solution).

Adhesive compositions comprising chitosan or derivatives thereof have been reported in the art.

For example, Ono K. et al. (Journal of biomedical materials research, 2000, 49, 289-295) describe a chitosan containing both azide and lactose moieties (Az-CH-LA) which is then photocrosslinked by application of an ultra-violet (UV) irradiation resulting in an insoluble hydrogel. The modified chitosan (Az-CH-LA) requires illumination with UV light for generating highly reactive nitrene groups that will react with each other or with amino groups of the chitosan (or tissue proteins) resulting in covalent linkage (chemical cross-links) between molecules or with tissue proteins providing adhesive properties. A composition containing the photochemically cross-linked insoluble hydrogel in water showed adhesive properties comparable to fibrin glues when tested in experiments consisting in testing the adhesion of two pieces of ham together.

In another example, US 2005/0112182 provides a N-alkyl chitosan derivative having an ultra-violet ray-curable functional group capable of forming a polymer upon irradiation with ultra violet rays usable as an adhesive or a film or a covering agent.

Chitosan, chitin and chitin-glucan copolymers are natural polysaccharides of great technological importance, as there are easily available in massive amounts, and as they present unique characteristics often not found for synthetic. Chitin is the main component of insect and crustacean cuticulum, and is also part of the cell walls of fungi and other organisms. Chitin is the linear polymer of N-acetyl-(D)-glucosamine linked through a β(1.4) osidic bond, that can be represented by Formula I.

Formula I: chitin

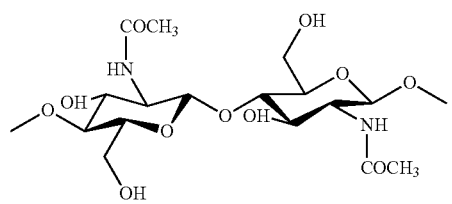

Chitosan is the random copolymer of N-acetyl-(D)-glucosamine and (D)-glucosamine linked by β(1-4)glucosidic bonds, that can be represented by Formula II. Chitosan is obtained by N-deacetylation of chitin.

Formula II: chitosan

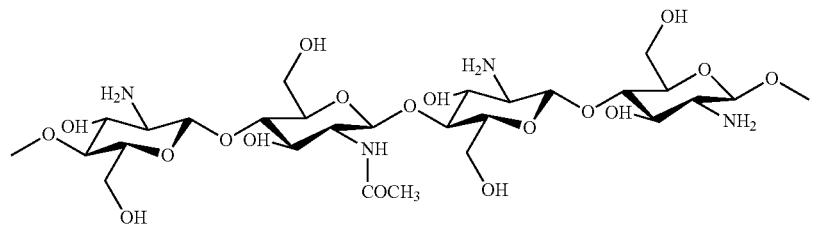

Chitin and chitosan polymers may be linked to or associate with glucan.

An important problem of some of the above-mentioned prior art adhesive compositions is however that they do not allow the compositions to be detached and/or repositioned, e.g. onto a living tissue or organ. However, there is a great need for a physician or practitioner to correct, if needed, the position of adhesive compositions or a material coated with such composition without compromising the adhesive strength and without provoking visible damage to the tissue or organ to which the adhesive composition or the material is attached.

Another disadvantage of prior art adhesive compositions is that the compositions often require manipulations such as UV irradiation or the mixing of multiple components for the composition to become adhesive. This is not practical and sometimes even impossible in a surgical setting.

Furthermore, it is not always possible with prior art adhesive compositions to adequately control their adhesive strength. Increasing or changing the adhesive strength of prior art compositions is generally done by increasing the pressure to apply the adhesive composition on a tissue or organ. However, this may cause unwanted damage to such tissues or organs.

In view of the above, there remains a great need in the art for improved adhesive compositions which can overcome at least one or more of the above-indicated problems.

SUMMARY

The present invention aims to overcome one or more of the above-indicated drawbacks of prior art adhesive compositions and provides biocompatible, resorbable, removable, or removable and repositionable adhesive compositions. The Applicant has found that by combining relatively high amounts of a chitin and/or chitosan containing material with a polar solvent, e.g. water, a composition can be obtained that is highly adhesive. Moreover, in particular embodiments, the present adhesive compositions have the important effect of being not only removable but also repositionable. This is highly unexpected, especially in view of the good adhesive properties of the compositions.

Thereto, in a first aspect, the invention provides adhesive compositions, wherein said compositions are removable and repositionable and comprise more than 10 wt %, and for instance more than 15 wt % of a chitin and/or chitosan containing material provided in a polar solvent, preferably water. The compositions of the present invention have the advantage that they do not require photochemical cross-linking to obtain their adhesive properties. Thus, more particularly in the compositions according to the present invention the chitin and/or chitosan containing material is not photochemically cross-linked.

In particular embodiments the invention provides an adhesive composition, wherein said composition has an adhesive shear strength between two supports of at least 0.1 Newton (N) as measured by a lap-shear testing method based on ASTM F2255-03.

In particular embodiments the invention provides adhesive compositions, wherein said chitin and/or chitosan containing material comprises or consists of a compound selected from the group comprising chitin, chitin-glucan, chitosan, chitosan-glucan, derivatives thereof, and any combinations thereof. Optionally, the compound is at least partially but non-photochemically cross-linked.

In particular embodiments the invention provides adhesive compositions, wherein said chitosan derivatives or said chitosan-glucan derivatives comprise chitosan polymers or chitosan-glucan copolymers that are covalently coupled to functional groups. In further particular embodiments the invention provides adhesive compositions, wherein the chitin derivatives or chitin-glucan derivatives comprise chitin polymers or chitin-glucan copolymers that are covalently coupled to functional groups.

In more particular embodiments compositions are provided wherein the chitosan derivatives comprise polymers comprising glucosamine monomers and N-acetyl-glucosamine monomers and wherein said chitosan-glucan derivatives comprise glucosamine monomers, N-acetyl-glucosamine and glucose monomers whereby at least some of said monomers are coupled to functional groups; and wherein said chitin derivatives comprise polymers comprising N-acetyl-glucosamine monomers, and wherein said chitin-glucan derivatives comprise N-acetyl-glucosamine monomers and glucose monomers whereby at least some of said monomers are coupled to functional groups.

In further particular embodiment the invention provides adhesive compositions wherein between 1 and 90% of the N-acetyl-glucosamine and/or glucosamine monomers of said chitosan polymers or wherein between 1 and 90% of the N-acetyl-glucosamine and/or glucosamine monomers and/or glucose monomers of said chitosan-glucan copolymers are coupled to said functional groups. In further particular embodiments the invention provides an adhesive composition wherein between 1 and 90% of the N-acetyl-glucosamine monomers of said chitin polymers or wherein between 1 and 90% of the N-acetyl-glucosamine monomers and/or glucose monomers of said chitin-glucan copolymers, are coupled to said functional groups.

In particular embodiments the functional groups are hydrophobic polymers selected from the group comprising aliphatic polyesters, aromatic polyesters, aliphatic polyamides, alkene homopolymers such as e.g. ethylene or propylene polymers, alkene copolymers such as e.g. ethylene and propylene copolymers, polycarbonates, polyacrylates and any combinations thereof.

In particular embodiments the invention provides adhesive compositions, wherein said chitosan derivatives or said chitosan-glucan derivatives respectively are chitosan polymers or chitosan-glucan copolymers that are covalently coupled to aliphatic polyesters, and in particular to polylactic acid (PLA). In further particular embodiments the invention provides adhesive compositions wherein said chitosan polymers coupled to polylactic acid consist of polymers comprising N-acetyl-glucosamine monomers, glucosamine monomers, and lactic acid monomers, wherein the ratio of (I) total number of lactic acid monomers to (II) total number of N-acetyl-glucosamine monomers and glucosamine monomers is comprised between 0.1 and 1000; and wherein said chitosan-glucan copolymers coupled to polylactic acid consist of polymers comprising N-acetyl-glucosamine monomers, glucosamine monomers, glucose monomers, and lactic acid monomers, wherein the ratio of (I) total number of lactic acid monomers to (II) total number of N-acetyl-glucosamine monomers and glucosamine monomers and glucose monomers is comprised between 0.1 and 1000.

In particular embodiments the invention provides adhesive compositions, wherein said chitin derivatives or said chitin-glucan derivatives respectively are chitin polymers or chitin-glucan copolymers that are coupled to aliphatic polyesters, and in particular to polylactic acid (PLA).

In more particular embodiments the invention provides adhesive compositions wherein said chitin polymers coupled to polylactic acid consist of polymers comprising N-acetyl-glucosamine monomers and lactic acid monomers wherein the ratio of (I) total number of lactic acid monomers to (II) total number of N-acetyl-glucosamine monomers is comprised between 0.1 and 1000; and wherein said chitin-glucan copolymers coupled to polylactic acid consist of polymers comprising N-acetyl-glucosamine monomers, glucose monomers and lactic acid monomers, wherein the ratio of (I) total number of lactic acid monomers to (II) total number of N-acetyl-glucosamine monomers and glucose monomers is comprised between 0.1 and 1000.

In further particular embodiments the invention provides adhesive compositions, wherein said polylactic acid has a degree of polymerization i.e. a number of lactic acid monomers per polylactic acid, which is lower than 1000.

In particular embodiments the invention provides adhesive compositions, wherein said chitosan derivatives or said chitosan-glucan derivatives respectively are chitosan polymers or chitosan-glucan copolymers that are covalently coupled to aminoalkyl, more particularly to aminoethyl.

The chitin and/or chitosan containing material of the adhesive compositions according to the invention can be provided in any form and even in multiple different forms. In particular embodiments the invention provides adhesive compositions, wherein said chitin and/or chitosan containing material is provided in the form of granules. Preferably the granules have an average granule size which is lower than 1000 µm, preferably lower than 500 µm and for instance comprised between 10 and 250 µm or between 30 and 150 µm.

In further particular embodiments, the invention provides adhesive compositions, which, comprise more than 10 wt % of a chitin and/or chitosan containing material provided in a polar solvent and further comprise at least one adhesive-enhancing agent, wherein said agent is provided in the form of granules. More particularly said adhesive-enhancing agent is provided in the form of granules having an average granule size which is lower than 1000 µm, preferably lower than 500 µm and for instance comprised between 10 and 250 µm or between 30 and 150 µm.

In further particular embodiments, the invention provides adhesive compositions wherein adhesive-enhancing agent is present in said composition in an amount of up to 60 wt %.

In particular embodiments, the invention provides adhesive compositions comprising said adhesive agent, wherein said adhesive-enhancing agent comprises a chitin and/or a chitosan containing material as defined herein. In preferred embodiments, said adhesive-enhancing agent consists of granules of chitin and/or of chitin-glucan.

The inventors have identified that adhesive compositions comprising more than 10 wt % of a chitin and/or chitosan containing material provided in a polar solvent overcome problems related to the absence of removability or removability/repositionability of adhesive compositions or sealants known in the prior art. This unexpected property allows for the use of such compositions as removable and repositionable adhesive compositions. Moreover, the present adhesive compositions have the important advantage of being suitable for use in humid/wet environments. Adhesive compositions according to the invention are able to adhere onto living tissues or organs in wet/humid environments. Unexpectedly, their adhesive characteristics such as e.g. adhesive strength, adhesion rate, removabililty/repositionability, period of time allowing removability/repositionability, number of subsequent removal/repositioning cycles, etc. . . can be controlled in function of the chitin and/or chitosan containing material comprised in the adhesive composition, e.g. in function of the type of material, its amount, and/or its application form.

Adhesive compositions according to the present invention advantageously fulfill one or more of the following criteria including
(i) an initial tack and an ability to bind to the tissue rapidly;
(ii) a good adhesion strength sufficient for the sealed tissues, or a matrix coated therewith and fixed onto the tissue not to move away;
(iii) biocompatibility, and even preferentially both biocompatibility and bioresorbability, biodegradability,
(iv) absence of toxicity of the adhesive composition or their degradation products and
(v) ease of use of the adhesive composition both directly on the site of application and for its spreading or impregnation properties onto/into a substrate or matrix; for instance for spreading onto/impregnating into a mesh.

Compositions according to the invention are able to be removed and repositioned, and therefore permit a practitioner to improve the position of the tissues to be sealed or to better adjust the correct position of a device to be fixed on a tissue.

The compositions according to the invention are further in particular embodiments able to fill gaps between two or more substrates; for instance between two parts of a tissue, between two different tissues, between a tissue and a surgical aid or device or an implant such as screws, pins, mesh, prosthesis etc. They are also able to form a barrier through the physical properties of the adhesive itself and by adhesion to a substrate. Advantageously, the adhesive compositions according to the invention maintain their sealing and adhesive properties for the expected lifetime of those materials.

In another aspect, the invention also provides matrices comprising an adhesive composition as described herein. The invention thus discloses matrices that are covered, coated, filled or impregnated by an adhesive composition as described herein. Such matrices may be selected e.g. among membranes, sheets, woven meshes, non-woven meshes, sponges, hemostatic sponges, yarns, surgical staples, prostheses, bandages and any combinations thereof and any other medical device to be fixed to a tissue in a wet/humid environment and for which repositioning during surgery may be needed.

The present invention further relates to methods for the preparation of adhesive compositions or matrices as defined herein as well as to their use in the field of surgical aids for closing openings, filling gaps, sticking or sealing two living tissues together or a living tissue to any other substrate such as an implantable material including membranes, meshes, prostheses, yarns, staples, screws, pins and the like.

Therefore in yet another aspect, the invention also relates to compositions according to the invention or matrices according to the invention for use as a medicament, and in particular for use as a surgical aid, or for use as a medical or surgical glue.

The invention also relates to compositions according to the invention or a matrix according to the invention for treating wounds, tissues or organs, e.g. by adhering said composition or said matrix to said wounds tissue or organs. In other words, the invention relates to a composition according to the invention or a matrix according to the invention for the preparation of a medicament for treating wounds, tissues or organs.

The invention also relates in another aspect, to the chitin and/or chitosan containing material as defined herein and to uses thereof.

The present invention further relates to the use of an adhesive-enhancing agent as defined herein in a composition or in an adhesive composition, preferably in a medical or surgical glue. Preferably, the invention relates to the use of an adhesive-enhancing agent as defined herein in an adhesive composition as defined herein.

With the insight to better show the characteristics of the invention, some preferred embodiments and examples are described hereafter referring to the enclosed drawings.

DESCRIPTION OF THE FIGURES

FIG. 4a shows the adhesiveness of these adhesive compositions on a porcine skin substrate on a first site of adhesion. FIG. 4a shows the adhesiveness of these adhesive compositions after repositioning on a second site of adhesion of a porcine skin substrate. The first and the second site of adhesion after repositioning are the same.

DETAILED DESCRIPTION OF THE INVENTION

Adhesive Composition

Figure 1A:
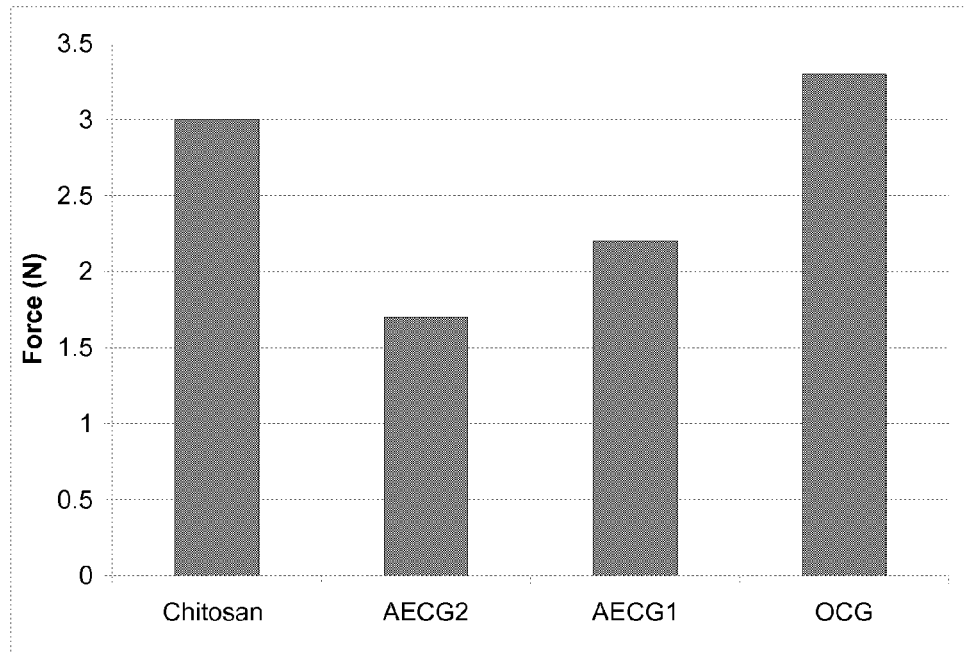
FIG. 1 illustrates adhesiveness of embodiments of adhesive compositions according to the invention on glass (FIG. 1a), ham (FIG. 1b) and porcine skin tissue (FIG. 1c).
Figure 1:
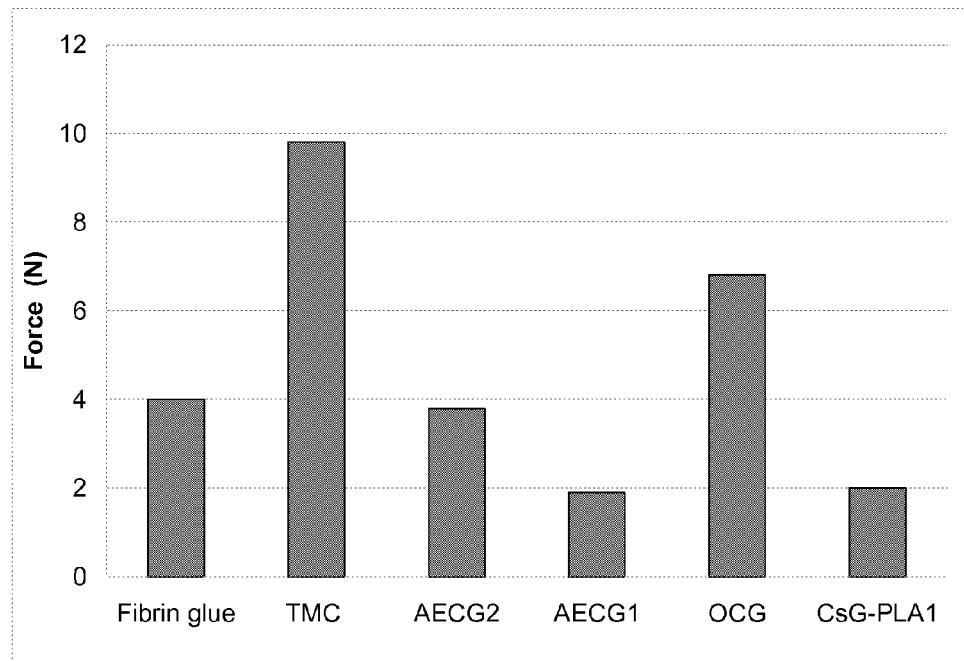
Figure 1:
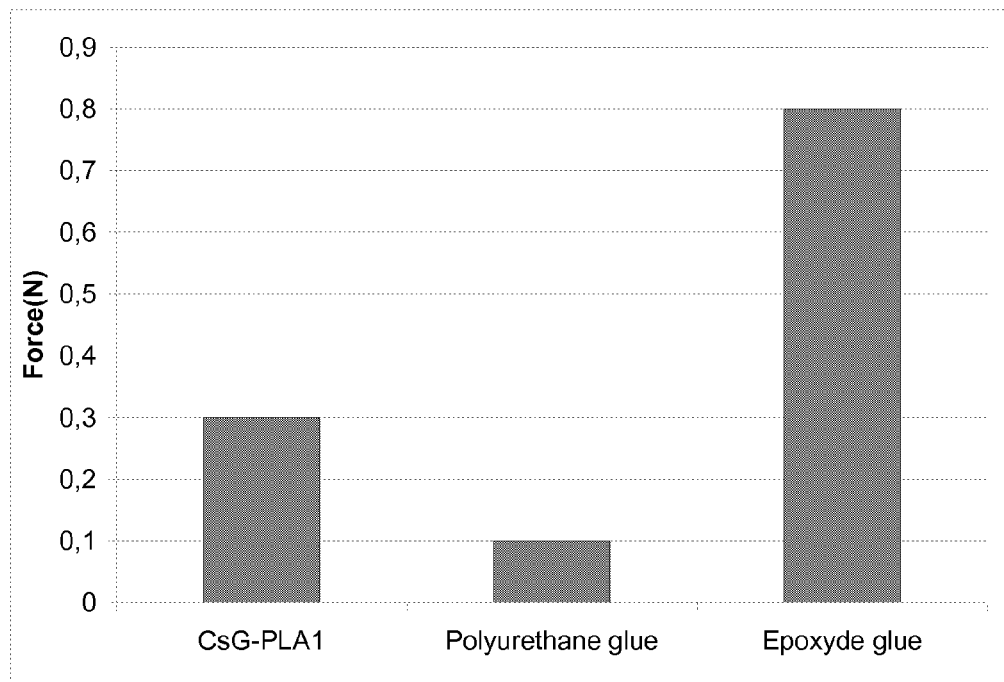

In a first aspect, the invention provides compositions comprising a chitin and/or chitosan containing material provided in a polar solvent. In particular, the invention provides a composition wherein said composition is removable and repositionable and comprises a chitin and/or chitosan containing material provided in a polar solvent. In another particular embodiment, the invention provides a composition which is removable and repositionable and which comprises a defined amount of a chitin and/or chitosan containing material, preferably more than 10% by weight of the composition, provided in a polar solvent, preferably in water. The fact that said composition is repositionable provides for particular advantages and applications in the medical field.

In particular embodiments, the present invention relates to a composition comprising a chitin and/or chitosan containing material which composition is removable without said chitin and/or chitosan containing material being photochemically cross-linked. The composition itself already provides the required adhesive properties without the necessity of photochemical cross-linking.

The term "chitin and/or chitosan containing material" refers to a "chitin containing material", a "chitosan containing material" or any combinations thereof.

The term "chitin and/or chitosan containing material" intends to refer to a material comprising or consisting of a compound that is selected from the group comprising chitin, chitin-glucan, chitosan, chitosan-glucan, chitin derivatives, chitin-glucan derivatives, chitosan derivatives, chitosan-glucan derivatives, and any combinations or mixtures thereof. Any of said compounds may optionally be non-photochemically cross-linked according to the methods well-known to a person skilled in the art. Moreover, any of said compounds may be provided in any suitable form (see further below).

In a particular embodiment, the present invention relates to a composition comprising a chitin and/or chitosan containing material which composition is removable without said chitin and/or chitosan containing material being photochemically cross-linked. Moreover, said chitin and/or chitosan containing material does not comprise any photoreactive groups such as azide groups.

The term "chitin containing material" may comprise a compound selected from the group comprising chitin, chitin-glucan, chitin derivatives, chitin-glucan derivatives and any combinations or mixtures.

Any of said compounds may be present in the adhesive composition in a form which is at least partially cross-linked according to methods well-known to a person skilled in the art.

The term "chitosan containing material" may comprise a compound selected from the group comprising chitosan, chitosan-glucan, chitosan derivatives, chitosan-glucan derivatives, and any combinations or mixtures. As indicated above, any of said compounds may optionally be cross-linked prior to use according to methods well-known to a person skilled in the art. In particular embodiments the compounds are not photochemically cross-linked, but may be chemically cross-linked by other means. In particular embodiments however the compounds are not chemically cross-linked. More particularly they are non-chemically cross-linked.

The terms "chitin" and "chitin polymers" are used herein as synonyms. In addition, the terms "chitosan" and "chitosan polymers" are used herein as synonyms. In addition, the terms "chitin-glucan" and "chitin-glucan copolymers" are used herein as synonyms. Also, the terms "chitosan-glucan" and "chitosan-glucan copolymers" are used herein as synonyms.

The term "chitin polymers" refers to chitin polymers that contain more than 10% of chitin, and preferably more than 40% of chitin. The term "chitin-glucan" refers to polymers, which comprise chitin polymers as well as glucan polymers in certain relative amounts. In the context of the present invention the terms "chitin" and "chitin-glucan" may be used interchangeably.

The term "chitosan-glucan polymers" refers to polymers, which comprise chitosan polymers as well as glucan polymers in certain relative amounts. In the context of the present invention the terms "chitosan" and "chitosan-glucan copolymers" may be used interchangeably. There is no restriction towards the molecular weight or the degree of deacetylation of the chitosan applied in the present invention.

The chitin, chitin-glucan, chitosan, chitosan-glucan, chitin derivatives, chitin-glucan derivatives, chitosan derivatives, chitosan-glucan derivatives, applied in the present invention may be obtained according to techniques known in the art from a source selected from the group comprising fungal source, yeast source, insect source, crustacean source, algae, microalgae including diatoms and any combinations thereof.

The term "cross-linked" intends to refer to the presence of links or bonds within (intra) and between (inter) chain(s) of the molecules, e.g. chain(s) of chitin, chitin-glucan, chitosan, chitosan-glucan, chitin derivatives, chitin-glucan derivatives, chitosan derivatives, chitosan-glucan derivatives; leading to a 3D network.

Different types of cross-linking are known in the art.

Chemical cross-linking implies the production of covalent bonds between polymers. Chemical cross-links can be formed by cross-linking reagents and/or are initiated by heat, pressure or radiation. In particular embodiments, the compounds present in the composition according to the present invention are compounds which are not photochemically cross-linked. More particularly the compounds do not require a reaction initiated by illumination with for instance UV light to ensure adhesive property of the composition.

In further particular embodiments, the compounds are not chemically cross-linked and do not require a reaction initiated by heat, pressure or radiation or mixture with a cross-linking agent to ensure adhesive property of the composition.

In physical cross-linking, dissolution is prevented by physical interaction which exists between different polymer chains, which is different from chemical cross-linking where covalent bonds are present between different polymer chains. Physical cross-linking avoids the use of cross-linking agents. In physical cross-linking, polymers form a cross-linked network with, i.e. counter-ion at the surface. In particular embodiments the compounds comprised in the compositions of the invention have been at least partially cross-linked prior to use, more particularly with a counter-ion, e.g. glycerol-phosphate disodium salt, tripolyphosphate (TPP) or sodium sulphate. Such ionic (physical) cross-linking results in a biocompatible cross-linked chitin polymers.

As such, the compositions according to the present invention are suitable for direct use, without the need to initiate cross-linking during use, such as e.g. by UV-irradiation. In addition, the present invention envisaged compositions comprising compounds having different degrees of cross-linking, i.e. compounds which are only partially cross-linked are also envisaged.

The term "derivatives" intends to refer to a chemically modified polymer. Chitin polymers, chitin-glucan copolymers, chitosan polymers, chitosan-glucan copolymers are polymers that can be modified chemically to obtain derivatives, according to techniques known by a person skilled in the art.

In an embodiment adhesive composition according to the invention comprises more than 5 wt % of a chitin and/or chitosan containing material as defined herein which is provided in a polar solvent, e.g. water. In another embodiment, said adhesive composition comprises more than 6 wt % of a chitin and/or chitosan containing material as defined herein, and for instance more than 7.5 wt %, more than 10 wt %, or more than 20 wt %. In an example, said adhesive composition comprises between 12 and 50 wt % or 15 to 35 wt % of a chitin and/or chitosan containing material as defined herein. In particular embodiments said chitin and/or chitosan containing material is adhesive without being photochemically cross-linked. In further particular embodiments the chitin and/or chitosan containing material is at least partially cross-linked, but non-photochemically cross-linked.

The term "wt %" as used herein intends to be synonym with "% by weight of a composition".

A polar solvent as used in a composition as defined herein can be selected from the group comprising water, ethanol, methanol, propanol, etc. . . . Preferably the amount of a polar solvent, e.g. water, provided in an adhesive composition according to the invention is higher than 10 wt % or higher than 25 wt % and for instance is comprised between 40 and 94 wt % or between 50 and 75 wt % of water.

In the present invention, the term "adhesive composition" means any composition that is able to stick to a site of application (also called site of administration). This term also includes a composition as defined herein that is able to and used to coat, cover or impregnate a matrix such as a surface or a substrate, whether natural or synthetic, and preferably a surface or substrate suitable for or being adhered to a living tissue or to an organ of a subject, both internally and externally.

In the present invention, the term "site of application" or "site of administration" means any surface to which an adhesive composition as defined herein or a matrix as defined herein that is covered or coated by an adhesive composition as defined herein adheres or sticks. More particularly, the site of application or site of administration may include a tissue or organ, located internally, i.e. in the interior of a subject's body, or externally i.e. at the surface of a subject's body, or may include any other surface whether natural or synthetic that can be positioned in the interior of a subject's body or at its surface, such as e.g. but not limited to a prosthesis, a membrane, a sheet, a woven or non-woven mesh, sponges for absorbing biological fluids, haemostatic sponges, bandages, yarns, staples and the like, for which the use of an adhesive composition is needed.

A "subject" as used herein is generally a human subject, although as will be appreciated by those in the art that the patient may be animal as well. Thus other animals, including mammals such cats; dogs; rabbits; farm animals including cows, horses, goats, sheep, pigs; as rodents including mice, rats, hamsters and guinea pigs; primates including monkeys, chimpanzees, orangutans and gorillas, are included within the definition of subject.

The term "adhesive" as used herein in the context of the present composition intends to refer to a composition that is capable of sticking to the site of topical application or administration and includes, but is no limited to, mucoadhesives, pressure-sensitive adhesives, i.e. which adhere upon application of pressure; moistenable adhesives, which adhere in the presence of water; and tacky or sticky type adhesives, which adhere upon immediate contact with a surface.

Adhesiveness of a composition can be measured in accordance with the invention with the hereunder described test procedure. The test procedure is based on the lap-shear testing method described by the procedure edited in ASTM F2255-03 "Standard test method for strength properties of tissues adhesives in lap-shear by tension loading". The ASTM F2255-03 is a standard test method for strength properties of tissue adhesives in lap-shear by tension loading. This test method is intended to provide a means for comparison of the adhesive strengths of tissue adhesives intended for use as surgical adhesives or sealants, or both, on soft tissue.

In the present procedure, two supports are glued together by means of an adhesive composition to be tested and the adhesive shear strength to disrupt the adhesive joint is then determined as the maximum force expressed in Newton (N) needed to separate the two supports.

Practically, two supports are glued at 37° C. as described in the ASTM F2255-03 test for a suitable period of time with the adhesive to be tested. Then the upper support is separated from the lower one at a constant rate of 5 mm/minute using a mechanical analyzer instrument (e.g. an Instron R (serie number 5566 (model)) until the adhesive joint disrupted. The adhesive shear strength is then determined as the maximum force (expressed in Newton (N)) needed for separation of the two supports.

More in particular, the experiments performed for measuring the adhesiveness of the adhesive compositions as described herein were based on the Standard Test Method ASTM F2255-03 for 'Strength Properties of Tissue Adhesives in Lap-Shear by Tension Loading' which was slightly adapted.

In the present invention, the following steps were used.

1. Selection of the tissue test samples. Model tissues were selected among samples of ham and samples of porcine skin tissue plentifully rinsed with a phosphate buffer at pH 7.2 prior to their use.

Samples of those model tissues were selected in areas of uniform thickness (max 5 mm) and of uniform surface smoothness and cut into 5 cm$^2$ pieces (2 cm×2.5 cm) with a fresh scalpel blade. The back-side of the tissue samples was strongly fixed at one of the ends of a glass support (2.5 cm×7.5 cm) by means of cyanoacrylate glue.

In some experiments, the adhesion compositions were tested without using ham or porcine skin tissue and were directly spread on the glass surface (5 cm$^2$).

2. For performing the adhesive strength test, two such glass supports ended with the test samples were prepared. The adhesive composition (approximately 200 mg) to be tested was uniformly spread onto the 5 cm$^2$ area of one of the two tissues samples, the other being left untreated.

3. The two tissue samples (one treated and the other untreated) fixed at the ends of the glass supports were then carefully superimposed until contact using a mechanical press conditioned at 37° C. No pressure has been applied and bonding only resulted from the contact. The contact time (also named the conditioning time) was adaptable and was depending on the experiments (typically, but not limited to, 5 or 15 minutes). The adhesive strength tests were performed immediately after the conditioning time.

4. The adhesive strength of tested compositions was measured by means of the lap-shear testing method.

The testing machine used for measuring the adhesive strength of the adhesive compositions was a mechanical analyzer instrument of the constant-rate-of-crosshead-movement type such as the Instron R apparatus (model 5566). Such apparatus comprises a fixed member (the lower fixature) and a movable member (the upper fixature) to which bound glass supports of point 3 were firmly fixed.

Both fixatures were then separated at a constant rate of 0.5 mm/minute until the adhesive joint between the two glass supports disrupted. The adhesive shear strength was determined as the maximum force (expressed in Newton (N)) needed for the separation of the two supports to occur.

In an embodiment, the present composition has an adhesive shear strength (binding strength) between two supports of at least 0.1 N, and preferably of at least 0.2 and for instance comprised between 0.2 and 100 N as measured by the procedure described above.

In a particular embodiment, an adhesive composition according to the invention has an adhesive shear strength (binding strength) between two supports of porcine skin tissue having a size of 2.5 by 2 cm and an uniform thickness of about 5 mm of at least 0.2 Newton (N), and preferably of at least 0.5 N, or at least 1.0 N as measured by the procedure described above.

In another particular embodiment, an adhesive composition according to the invention has an adhesive shear strength (binding strength) between two supports of ham having a size of 2.5 by 2 cm and a uniform thickness of about 5 mm of at least 0.2 Newton (N), and preferably of at least 0.5 N as measured by the procedure described above.

In particular embodiments, the adhesive compositions according to the invention are "removable", meaning that they can be, if needed, removed from a surface on which they adhere without leaving visible damage of and/or substantial residue on the surface. This means for instance that adhesive compositions according to the invention or a matrix which is impregnated, coated or covered by such adhesive compositions can be removed from their site of application without leaving any visible damage thereto.

In further particular embodiments, the adhesive compositions according to the invention can not only be removed but also thereafter repositioned. Unexpectedly, it has been shown that adhesive compositions according to the invention keep adhesiveness, which may be a partial or a total adhesiveness, or which unexpectedly may even be increased adhesiveness, after having been removed from a site of application. In the present invention, a "repositionable" adhesive composition means any composition that is capable of maintaining partial or total adhesiveness or that is even capable of increased adhesiveness after at least one application cycle. Such an application cycle typically comprises, in a first step, sticking the adhesive composition to the site of application, followed by, in a second step, removing it without provoking visible damage to the site of application. According to the present invention, the repositioning comprises, in addition to the first and the second step, in a third step, sticking the same adhesive composition again either at the same site of application or on another site of application.

The adhesive compositions of the invention enable the user to reposition either the adhesive compositions or a matrix which is covered, coated or impregnated by said adhesive compositions during a period of at least 2 minutes, or of at least 5 minutes or preferably at least 10 minutes. This allows a user, if needed, to remove, reposition and fix again by adhesion, either the adhesive compositions as such as defined herein or a matrix covered, coated or impregnated by such composition.

In particular embodiments, adhesive compositions as described herein are provided which can advantageously be used in a wet or humid medium or environment. In the present invention, the term "humid or wet" medium or environment means a medium or environment that is characterized by a certain degree of moisture (wet corresponding to 100%). This term will in the present context generally be applicable when referring to the use in/on a tissue or organ of a subject, both at internal or external sites of application in said subject. A humid or wet environment is thus typically found in the context of a tissue or organ, whereby such tissue may be an external tissue such as e.g. skin, nails, hair, lips, mucosal tissue and the like; or an internal tissue such as e.g. abdominal tissue, muscle, pelvic barriers, parietal membranes, corneal surface, nerves, tendons, ligaments, blood vessels, mucosal tissue and the like. Repositioning can be done in a wet or humid environment (see also below). Thus adhesive compositions according to the invention enable repeated fixation, said repeated fixation being possible in wet/humid environments. In another embodiment said adhesive composition is biocompatible, and preferably also bioresorbable or biodegradable, i.e. it can be broken down by the body and does not require mechanical removal.

In the present invention, the term "biocompatible" composition refers to a composition that comprises "biocompatible polymers", i.e. polymers that perform their desired function with respect to a medical therapy without eliciting any undesirable local or systemic effects.

The term "biodegradable" or "bioresorbable" composition as used herein refers to a composition that comprises "biodegradable polymers" or bioresorbable polymers", i.e; polymers that disappear, or that are eliminated by a subject's body after a certain period of time after having been in contact with a living material, whether by minute, partial or total degradation of the polymer into (i) monomers, (ii) parts of them, (iii) oligomers or polymers of the same nature as the initial biodegradable polymer but having a lower mass, (iv) small molecules whose nature is different from the original polymer but that originate from the degradation and/or metabolization of the original polymer.

Derivatives

As mentioned above, the "chitin and/or chitosan containing material" as applied in the present compositions may include derivatives of chitin and/or chitosan compounds such as chitin derivatives, chitin-glucan derivatives, chitosan derivatives, chitosan-glucan derivatives, and any combinations or mixtures thereof.

In particular embodiments, adhesive compositions are provided wherein chitin derivatives comprise chitin polymers comprising N-acetyl-glucosamine monomers, wherein at least some of said monomers are coupled to one or more than one functional group, which in the latter case can be the same or different. In further embodiments, adhesive compositions are provided wherein chitin-glucan derivatives comprise chitin-glucan copolymers comprising N-acetyl-glucosamine monomers and glucose monomers, wherein at least some of said monomers are coupled to one or more than one functional group, which in the latter case can be the same or different.

In further embodiment, compositions are provided wherein chitosan derivatives comprise chitosan polymers comprising glucosamine monomers and N-acetyl-glucosamine monomers, wherein at least some of said monomers are coupled to one or more than one functional group, which in the latter case can be the same or different. In yet further particular embodiments, compositions are provided wherein chitosan-glucan derivatives comprise chitosan-glucan copolymers comprising glucosamine monomers and N-acetyl-glucosamine monomers, and glucose monomers, wherein at least some of said monomers are coupled to one or more than one functional group, which in the latter case can be the same or different.

Chemical modification can for instance be carried out in the above polymers on one or more functional moieties of either the N-acetyl-glucosamine units, e.g. the alcohol moieties, and/or of the glucosamine units, e.g. the alcohol moieties and/or amine moieties and/or of the glucose units, e.g. the alcohol moieties.

Functional Groups

In particular embodiments, the functional groups present on said chitin and/or chitosan containing material of the compositions according to the present invention are selected from the group comprising but not limited to hydrophobic functional groups, hydrophilic functional groups, ionic functional groups and any combination thereof.

In further particular embodiments, the hydrophobic functional groups are selected from the group consisting of alkyl groups, alkenyl groups, araalkyl groups, alkaryl groups, and combinations thereof having between 1 and 100 carbon atoms, and for instance between 1 and 50, or 1 and 25 or 1 and 10 carbon atoms, where one or more of carbon atoms of the groups may be replaced by a hetero atom and/or hetero atom moieties selected from the group comprising boron atoms, nitrogen atoms, oxygen atoms, sulfur atoms, silicon atoms, germanium, ester moiety, amide moiety, urea moiety, urethane moiety, and combinations thereof and where one or more of the hydrogen atoms may be replaced by a hetero atom and/or hetero atom moieties selected from the group comprising halogen atoms, an alkoxide groups, an amide group, and combinations thereof.

In yet further particular embodiments, the hydrophobic functional groups are selected from the group comprising carboxyl acids, organo sulfonic acids, polyethers, polyether amines, polyesters, sterols, porphyrins and combinations thereof.

In yet further particular embodiments, the hydrophilic functional groups are selected from the group comprising diamines, polyamines, diols, polyols, diacids, polyacids, crown ethers, glymes, polyalkenylethers, polyalkenylamines, polyalkenyletheramines, polyacrylic acids, polyvinylacohols, and combinations thereof.

In yet further particular embodiments, the ionic functional groups are selected from the group comprising a metal salt, an ammonium salt, a phosphonium salt, a sulfate salt, a carboxylic acid salt, a phosphate salt, dicarboxylic acids, poly carboxylic acids, where one carboxylic acid is used to form a covalent linkage with chitosan and the other acid groups can take a charge, diamines, poly amines, where one amine is used to form a covalent linkage with chitosan and the other amino groups can take a charge, metal ions, ionic atomic clusters, ionic molecular structures, simple anions, polyatomic anions, deprotonated oxoacids, substituted deprotonated oxoacids or deprotonated organic acids where these groups interact with the chitosan via an electrostatic interaction, and mixtures or combinations thereof.

In particular embodiments, said functional group consists of an aminoalkyl. In an example said functional group consists of an aminoethyl.

In particular embodiments, the chitin and/or chitosan containing material as defined herein includes derivatives of chitosan and/or of chitin such as but not limited to:

- amino-alkyl derivatives, such as e.g. amino-ethyl chitin-glucan copolymer, amino-ethyl chitin, amino-ethyl chitosan and the like;
- N-alkyl or O-alkyl hydrophobised chitosan, chitosan-glucan, chitin, or chitin-glucan, such as e.g. ethanoyl, propanoyl, butanoyl, pentanoyl, hexanoyl, heptanoyl, octanoyl, nonaoyl, decanoyl, or dodecanoyl chitosan, chitosan-glucan, chitin, or chitin-glucan;
- positively charged chitosan or chitin derivatives such as trialkyl ammonium chitosan (TMC), e.g. with degrees of substitution (degree of quaternization) ranging from 1 to 90%; N-(2-hydroxy)propyl-3-trimethylammonium chitosan chloride and the like;
- negatively charged chitosan or chitin derivatives such as succinyl chitosan, N,O-carboxyalkyl chitosan, N,O-sulfoalkyl chitosan and the like, the charge of which being often pH dependent due to the pKa of the acido-basic function added to chitosan.
- neutral chitosan or chitin derivatives such as for example N,O-acetyl chitosan, N,O-alkyl chitosan, ethanoyl, propanoyl, butanoyl, pentanoyl, hexanoyl, heptanoyl, octanoyl, nonaoyl, decanoyl, dodecanoyl and the like chitosan or chitin derivatives;
- zwitterionic chitosan and chitin derivatives thus meaning chitosan or chitin derivatives bearing permanent anionic and cationic functions or non-permanent anionic and cationic functions depending on the pH;
- chitosan and chitin grafted with (i.e. covalently bound to) hydrophobic polymers, such as e.g. aliphatic polyesters such as homopolymers and copolymers of lactic acid, glycolic acid, epsilon-caprolacton and p-dioxanone; aliphatic and/or aromatic polyesters; aliphatic polyamides; ethylene polymers and copolymers; polypropylene polymers and copolymers; polycarbonate; polyacrylates and the like.

In particular embodiments, the term "a chitin and/or chitosan containing material" as defined herein includes derivatives of chitosan and/or of chitin such as those defined herein which are blended (i.e. mixed) with hydrophobic polymers, such as e.g. aliphatic polyesters (such as e.g. homopolymers and copolymers of lactic acid, glycolic acid, epsilon-caprolacton and p-dioxanone); aliphatic and/or aromatic polyesters; aliphatic polyamides; ethylene polymers and copolymers; polypropylene polymers and copolymers; polycarbonate, polyacrylates and the like.

Non-limitative examples of aliphatic polyesters as given herein include but are not limited to homopolymers and copolymers of lactic acid, glycolic acid, epsilon-caprolacton and p-dioxanone.

Non-limitative examples of hydrophobic polymers as given herein include but are not limited to Polyacrylonitrile, Polybutadiene, Polycarbonates, Polychloroprene, Polycyanoacrylates, Polydicyclopentadiene, Polyesters, Poly(ether sulfones), Polyethylene, Polyimides, Polyisobutylene, Polyisoprene, Polyketones, Poly(methyl methacrylate), Poly(phenylene oxide), Poly(phenylene sulfide), Polypropylene, Polystyrene, Polytetrafluoroethylene, Polyurethanes, Poly(vinyl acetate), Poly(vinyl chloride), Poly(vinylidene chloride), Poly(vinylidene fluoride), Polyvinylpyrrolidone and the like.

Other derivatives that can be used in the present invention can be obtained through an O-substitution performed on the hydroxyl moiety of (i) either the glucosamine and/or N-acetylglucosamine monomer of chitosan or of (ii) the glucosamine and/or N-acetylglucosamine and/or glucose monomer of chitosan-glucan, or of (iii) the N-acetylglucosamine monomer of chitin or of (iv) the N-acetylglucosamine monomer and/or glucose monomer of chitin-glucan.

In particular embodiments, compositions are provided wherein said functional groups are hydrophobic polymers selected from the group comprising aliphatic polyesters, aromatic polyesters, aliphatic polyamides, alkene homopolymers such as e.g. ethylene or propylene polymers, alkene copolymers such as e.g. ethylene/propylene copolymers, polycarbonates, polyacrylates and any combinations thereof.

In further particular embodiments, compositions are provided wherein said functional groups are aliphatic polyesters, and in particular wherein said aliphatic polyester is polylactide.

The term polylactic acid (denoted as PLA) as used herein refers to chains of lactic acid molecules whatever their preparation method. Polylactic acid can be obtained either by a ring opening polymerization of lactide, either D,L-, L-, or D-lactide or by polycondensation of lactic acid. PLA chains can be grafted on (covalently coupled to) chitin or chitosan using methods that are well-known to a person skilled in the art.

Lactic Acid Functional Group

In particular embodiments the functional group present on the chitin and/or chitosan containing material of the compositions according to the invention consists of lactic acid. In more particular embodiments, the chitin and/or chitosan containing material as defined herein is selected from the group comprising chitin, chitin-glucan, chitosan and chitisosan-glucan that are each covalently coupled to one or more lactic acid molecules.

In further embodiments said chitin derivatives are chitin polymers to which one or more lactic acid molecules are covalently bonded. Such derivatives are also denoted herein as chitin-lactic acid (C-LA). In another embodiment, said chitin-glucan derivatives are chitin-glucan polymers to which one or more lactic acid molecules are covalently bonded. Such derivatives are also denoted herein as chitin-glucan-lactic acid (CG-LA). In yet further embodiments, said chitosan derivatives are chitosan polymers to which one or more lactic acid molecules are covalently bonded. Such derivatives are also denoted herein as chitosan-lactic acid (Cs-LA). In further embodiments, said chitosan-glucan derivatives are chitosan-glucan polymers to which one or more lactic acid molecules are covalently bonded. Such derivatives are also denoted herein as chitosan-glucan-lactic acid (CsG-LA).

Each N-acetyl-glucosamine or only a part of the N-acetyl-glucosamine of the chitin may be coupled to a lactic acid molecule. Similarly each N-acetyl-glucosamine and/or each glucose monomer or only a part of the N-acetylglucosamine and/or glucose monomers of the chitin-glucan copolymers may be coupled to a lactic acid molecule. In a preferred embodiment, a composition is provided wherein more than 1% and for instance between 5 and 90% or for instance between 10 and 75% of the N-acetyl-glucosamine monomers of said chitin or of the N-acetylglucosamine and/or glucose monomers of said chitin-glucan are coupled to said lactic acid.

Each glucosamine monomer and/or each N-acetyl-glucosamine monomer or only a part of these monomers of chitosan may be linked to a lactic acid. Similarly, each glucosamine monomer and/or each N-acetyl-glucosamine monomer and/or each glucose monomer or only a part of these monomers of the chitosan-glucan copolymers may be linked to a lactic acid. In a preferred embodiment, a composition is provided wherein more than 1% and for instance between 5 and 90% or for instance between 10 and 75% of the N-acetyl-glucosamine and/or glucosamine monomers of said chitosan or of the N-acetyl-glucosamine and/or glucosamine and/or glucose monomers of said chitosan-glucan copolymers are coupled to said lactic acid.

In particular embodiments, the invention provides an adhesive composition which comprises more than 5 wt %, and for instance more than 7.5 wt %, more than 10 wt %, or more than 20 wt %, of a chitin and/or chitosan containing material selected from the group comprising chitin-lactic acid; chitin-glucan-lactic acid; chitosan-lactic acid; chitosan-glucan-lactic acid and combinations thereof. More particularly, the amount of polar solvent, e.g. water, provided in such adhesive composition according to the invention is higher than 10 wt % or higher than 25 wt % and for instance is comprised between 40 and 94 wt % or between 50 and 75 wt %.

Polylactic Acid (PLA) Functional Group

In particular embodiments of the compositions according to the invention the functional group present on said chitin and/or chitosan containing material consists of polylactic acid (PLA).

In particular embodiments, the chitin and/or chitosan containing material as defined herein is selected from the group comprising chitin, chitin-glucan, chitosan and chitosan-glucan that are each covalently coupled to one or more chains of polylactic acid.

In further particular embodiments said chitin derivatives are chitin polymers that are covalently bonded to one or more polylactic acid chains (PLA). Such derivatives are also denoted herein as chitin-PLA derivatives. In more particular embodiments, said chitin-glucan derivatives are chitin-glucan copolymers to which one or more polylactic acid chains (PLA) are covalently bonded. Such derivatives are also denoted herein as chitin-glucan-PLA derivatives.

In particular embodiments said chitosan derivatives are chitosan polymers that are covalently bonded to one or more polylactic acid chains (PLA). Such derivatives are also denoted herein as chitosan-PLA derivatives (Cs-PLA derivatives). In further embodiments, said chitosan-glucan derivatives are chitosan-glucan copolymers that are covalently bonded to one or more polylactic acid chains (PLA). Such derivatives are also denoted herein as chitosan-glucan-PLA derivatives (CsG-PLA derivatives).

In particular embodiments, the invention provides an adhesive composition which comprises more than 5 wt %, and for instance more than 7.5 wt %, more than 10 wt %, or more than 20 wt %, of a chitin and/or chitosan containing material selected from the group comprising chitin-PLA; chitin-glucan-PLA; chitosan-PLA; chitosan-glucan-PLA and combinations thereof. Preferably the amount of polar solvent e.g. water, provided in such adhesive composition according to the invention is higher than 10 wt % or higher than 25 wt % and for instance is comprised between 40 and 94 wt % or between 50 and 75 wt % of water.

In particular embodiments, the chitin-PLA or chitin-glucan-PLA derivatives respectively consist of chitin or chitin-glucan copolymers having covalently bounded thereto chains of at least two lactic acid molecules. More particularly, the ratio of (I) total number of lactic acid monomers to (II) the total number of N-acetyl-glucosamine monomers of chitin or of N-acetyl-glucosamine and glucose monomers chitin-glucan is comprised between 0.1 and 1000, and for instance between 0.1 and 100 and even more preferably between 0.1 and 20.

In further particular embodiments, the Cs-PLA polymers or the CsG-PLA polymers respectively consist of chitosan or chitosan-glucan copolymers having covalently bounded thereto chains of at least two lactic acid molecules. Preferably, the ratio of (I) total number of lactic acid monomers to (II) the total number of glucosamine and N-acetyl-glucosamine monomers of chitosan or of glucosamine and N-acetyl-glucosamine and glucose monomers of chitosan-glucan is comprised between 0.1 and 1000, and for instance between 0.1 and 100 and even more preferably between 0.1 and 20.

The degree of polymerization (DP), i.e. the number of lactic acid monomers per PLA chain, of each individual PLA is more than 2, and for instance ranges from 2 to 1000, or from 2 to 100 or from 2 to 20. In another embodiment, a composition is provided wherein said PLA has a degree of polymerization i.e. a number of lactic acid monomers per PLA, which is lower than 1000, and preferably lower than 100, and for instance lower than 20.

The length of the PLA chain linked to the glucosamine monomers and/or N-acetyl-glucosamine monomers of chitosan or linked to the glucosamine monomers and/or N-acetyl-glucosamine monomers and/or glucose monomers of chitosan-glucan may be the same for all monomers or may be different for different monomers. Similarly, the length of the PLA chain linked to the N-acetyl-glucosamine monomers of chitin or to the N-acetyl-glucosamine monomers and/or glucose monomers of chitin-glucan may be the same for all monomers or may be different for different monomers.

Each N-acetyl-glucosamine monomer of chitin or each N-acetyl-glucosamine and/or glucose monomer of chitin-glucan may be coupled to a PLA chain or only a part of these monomers may be linked to a PLA chain. In a preferred embodiment, a composition is provided wherein more than 1% and for instance between 5 and 90% or for instance between 10 and 75% of the N-acetyl-glucosamine monomers of said chitin of the N-acetyl-glucosamine monomers and/or glucose monomers of said chitin-glucan are coupled to said PLA chains.

Similarly, each glucosamine monomer and/or each N-acetyl-glucosamine monomer and/or each glucose monomer of chitosan-glucan may be coupled to a PLA chain or only a part of these monomers may be linked to a PLA chain. Also each glucosamine monomer and/or each N-acetyl-glucosamine monomer of chitosan may be coupled to a PLA chain or only a part of these monomers may be linked to a PLA chain. In a preferred embodiment, a composition is provided wherein more than 1% and for instance between 5 and 90% or for instance between 10 and 75% of the N-acetyl-glucosamine and/or glucosamine and/or glucose monomers of said chitosan-glucan or of the N-acetyl-glucosamine and/or glucosamine monomers of said chitosan are coupled to said PLA chains.

Amino-alkyl Functional Group

In particular embodiments the functional group present on the chitin and/or chitosan containing material of the compositions according to the invention consists of an aminoalkyl, more particularly an amino-ethyl. In more particular embodiments, the chitin and/or chitosan containing material as defined herein is selected from the group comprising chitin, chitin-glucan, chitosan and chitosan-glucan that are each covalently coupled to one or more amino-alkyl, more particularly amino-ethyl molecules.

In further embodiments said chitin derivatives are chitin polymers to which one or more amino-ethyl molecules are covalently bonded. Such derivatives are also denoted herein as amino-ethyl chitin. In another embodiment, said chitin-glucan derivatives are chitin-glucan polymers to which one or more amino-ethyl molecules are covalently bonded. Such derivatives are also denoted herein as amino-ethyl chitin-glucan. In yet further embodiments, said chitosan derivatives are chitosan polymers to which one or more amino-ethyl molecules are covalently bonded. Such derivatives are also denoted herein as amino-ethyl chitosan. In further embodiments, said chitosan-glucan derivatives are chitosan-glucan polymers to which one or more amino-ethyl molecules are covalently bonded. Such derivatives are also denoted herein as amino-ethyl chitosan-glucan.

Each N-acetyl-glucosamine or only a part of the N-acetyl-glucosamine of the chitin may be coupled to a amino-ethyl molecule. Similarly each N-acetyl-glucosamine and/or each glucose monomer or only a part of the N-acetylglucosamine and/or glucose monomers of the chitin-glucan copolymers may be coupled to a amino-ethyl molecule. In particular embodiments, a composition is provided wherein more than 1% and for instance more than 5%, more than 10%, more than 20%, more than 30%, more than 40%, more than 50%, more than 60%, more than 70%, more than 80%, more than 90%, and even up to 100% of the N-acetyl-glucosamine monomers of said chitin or of the N-acetylglucosamine and/or glucose monomers of said chitin-glucan are coupled to said amino-ethyl.

Each glucosamine monomer and/or each N-acetyl-glucosamine monomer or only a part of these monomers of chitosan may be linked to an amino-ethyl. Similarly, each glucosamine monomer and/or each N-acetyl-glucosamine monomer and/or each glucose monomer or only a part of these monomers of the chitosan-glucan copolymers may be linked to an amino-alkyl such as an amino-ethyl. In particular embodiments, a composition is provided wherein more than 1% and for instance more than 5%, more than 10%, more than 20%, more than 30%, more than 40%, more than 50%, more than 60%, more than 70%, more than 80%, more than 90%, and even up to 100% of the N-acetyl-glucosamine and/or glucosamine monomers of said chitosan or of the N-acetyl-glucosamine and/or glucosamine and/or glucose monomers of said chitosan-glucan copolymers are coupled to said amino-alkyl, more particularly amino-ethyl.

In particular embodiments, the invention provides an adhesive composition which comprises more than 5 wt %, and for instance more than 7.5 wt %, more than 10 wt %, or more than 20 wt %, more than 30 wt %, more than 40 wt %, more than 50 wt %, more than 60 wt %, more than 70 wt %, more than 80 wt %, more than 90 wt %, and even up to 100 wt %, of a chitin and/or chitosan containing material selected from the group comprising amino-ethyl chitin; amino-ethyl chitin-glucan; amino-ethyl chitosan; amino-ethyl chitosan-glucan and combinations thereof. More particularly, the amount of polar solvent, e.g. water, provided in such adhesive composition according to the invention is higher than 10 wt % or higher than 25 wt % and for instance is comprised between 40 and 94 wt % or between 50 and 75 wt %.

In particular embodiments, chitin and chitosan derivatives comprised in adhesive compositions as defined herein are surface active which means that said derivatives, when solubilized in a solvent are able to reduce the surface tension of said solvent e.g., in the case of water below 72 mN/m at room temperature, preferably below 65 mN/m at room temperature for instance at a concentration of 1% (w/v).

In further particular embodiments, the chitin and/or chitosan containing material according to the invention may be present in any form and even in multiple different forms in said adhesive composition, depending on their application in various systems. For instance the chitin and/or chitosan containing material according to the invention may be present in a lyophilised or powdery form or in a liquid form, and for instance in the form of powder, fiber, solution, a gel, a hydrogel, a dispersion, a suspension, a paste, a foam, a film, granules, such as micro-, milli- or nano-granules. Said form can be obtained by techniques known by a person skilled in the art.

In more particular embodiments, said chitin and/or chitosan containing material is present in a granular form, and preferably in the form of granules or a powder. Even more preferably said chitin and/or chitosan containing material is provided in said adhesive composition in the form of granules having an average granule size (diameter) which is lower than 1000 µm, preferably lower than 500 µm and for instance comprised between 10 and 250 µm or between 30 and 150 µm.

The compositions according to the present invention are also optionally characterized by the following parameters either taken alone or in combination.

Adhesive compositions according to the invention are suitable for obtaining good adhesion within a time period ranging from a few seconds up to several hours. Preferably the adhesion time ranges within 1 second and 60 minutes, more preferably between 1 minute and 30 minutes. In other words, in another embodiment, the sticking rate of an adhesive composition according to the invention is inferior to 1 hour, preferably inferior to 30 minutes, most preferably comprised between a few seconds and 15 minutes. The "sticking rate", as used herein refers to the time needed for two surfaces to be glued together by using the adhesive composition of the invention so that a minimal force is needed, a.e. to separate them, e.g. a minimal force of 0.1 Newton (N) is needed as measured using a method based on ASTM F2255-03 test as indicated above.

Also, repositioning of an adhesive composition according to the invention is not limited to short periods of time after a first positioning and is still possible after periods of time of several seconds, several minutes and even several hours, thus comparable to the period of time needed by a physician for performing a first adhesion then a re-positioning. In practical situations, a period of time ranging from 1 to 60 minutes, preferably from 1 to 30 minutes seems to be adequate for re-positioning.

In particular embodiments, the invention provides an adhesive composition having a viscosity of at least 100 centipoise (0.1 Pa·s), and preferably of at least 1000 centipoise (1 Pa·s), at room temperature. Viscosity can be measured by rotational viscosimetry or by any other techniques known in the art.

In yet further embodiments, the invention provides an adhesive composition having a pH of at least 3.5, and for instance a pH of 4 to 8.

Addition of Other Components to the Adhesive Compositions

In particular embodiments, the compositions according to the invention can also include buffers, vehicles, additives, preservatives, excipients, adjuvants, or any other component that will render the composition particularly suitable for a particular purpose. For instance, adhesive compositions according to the invention may also comprise optional ingredients such as plasticizers, fillers, anti-oxidants or other agents well-known to the skilled person of the art. In any of the above compositions, any amounts of other components can be added to the compositions.

In particular embodiments, adhesive compositions are provided comprising at least one adhesive-enhancing agent. The term "adhesive-enhancing agent" as used herein refers to an agent that is capable of increasing the adhesiveness of a composition as defined herein. With the term "adhesiveness"

in this context is meant adhesiveness as defined herein which can be measured with the testing method described above.

Preferably said adhesive-enhancing agent is in the form of granules, which can be round, spherical or angular. The term "granules" as used herein is intended to refer to solid granules, and also includes powders.

In particular embodiments the adhesive-enhancing agent is provided in the form of granules having an average granule size which is lower than 1000 μm, preferably lower than 500 μm and for instance comprised between 10 and 250 μm or between 30 and 150 μm. Average granule size should be understood as meaning average diameter.

In further particular embodiments, said adhesive-enhancing agent, preferably said granules, is/are present in an adhesive composition as defined herein in an amount of up to 60 wt %, and for instance between 1 and 50 wt %, and for instance between 1 and 35 wt %, and for instance higher than 5 wt %, higher than 15 wt %, higher than 25 wt %, higher than 35 wt %, or higher than 45 wt %.

The applicants have surprisingly found that adhesiveness and other characteristics of compositions, of adhesive compositions and preferably of medical or surgical glues, more preferably of adhesive compositions according to the invention can be changed, modulated or fine-tuned by adding an adhesive-enhancing agent as defined herein. Adhesion strength of compositions, adhesive compositions and preferably medical or surgical glues, more preferably adhesive compositions according to the invention can be modified, thus lowered or enhanced, preferably enhanced, when granules, preferably micro-granules, are added to such adhesive compositions. The addition of the granules enables to reach adhesion strengths that are higher than glues or adhesive compositions lacking said granules and act thus as adhesion enhancer agents.

The addition of granules to adhesive compositions according to the invention or to any other composition preferably of medical or surgical glues also permits to shorten the time needed to reach acceptable adhesion strengths and thus are adhesion accelerators.

Unexpectedly, the addition of an adhesion enhancing agent as defined herein does not hamper removal and/or the removal/re-positioning of the adhesive compositions. The adhesion strength of the re-positioned adhesive composition or of the matrix treated, coated or impregnated by the adhesive composition comprising an adhesive-enhancing agent as defined herein is equal, lower or higher that the adhesion strength measured in the first adhesion step.

Another unexpected finding is that the adhesion strength of a re-positioned adhesive composition according to the invention comprising an adhesive agent as defined herein or of a re-positioned matrix coated or impregnated therewith is equal or even higher than the adhesion strength measured for a first adhesion. Addition of an adhesion enhancing agent as defined herein in granular form, maintains and even improves the ability to firstly position, then easily remove, and then to re-position and strongly fix such composition or matrix (for instance without additional pressure) because the adhesion strength is then equal or even higher than in the first positioning step.

For instance adhesive compositions according to the invention comprising an adhesive-enhancing agent as defined herein, and which adhesive-enhancing agent preferably is a chitin and/or chitosan containing material in the form of a granules as defined herein (see below), has, when repositioned an adhesive shear strength (binding strength) between two supports expressed in Newton (N) as measured by the lap-shear testing method as described above, which is at least 5%, and for instance at least 10, or 15% higher than the adhesive strength measured in a same way for said composition during a first positioning. Also, an enhancing agent in granular form as defined herein permits to lengthen the period of time allowing re-positioning. For instance, an adhesive composition without granules allows a re-positioning within a certain period of time, for instance within 10 minutes, while by addition of granules to the composition, this period of time will to be substantially lengthened. This gives a physician more time to correct the positioning of the adhesive composition or a matrix covered therewith.

In particular embodiments, said adhesive-enhancing agent is a chitin and/or chitosan containing material as defined herein, preferably in the form of granules, wherein said material is hygroscopic. The term "hygroscopic" as used herein is meant to refer to a material which is able to attract water molecules from the surrounding environment through absorption or adsorption.

In further particular embodiments, said adhesive-enhancing agent comprises a chitin and/or a chitosan containing material which is in the form of a powder or granules such as for instance the chitin-glucan micro-granules disclosed in WO2008061999, which is incorporated herein by reference.

In further particular embodiments, said adhesive-enhancing agent comprises a chitin and/or a chitosan containing material which is as defined above, i.e. a material comprising or consisting of a compound that is selected from the group comprising chitin, chitin-glucan, chitosan, chitosan-glucan, chitin derivatives, chitin-glucan derivatives, chitosan derivatives, chitosan-glucan derivatives, and any combinations or mixtures thereof as defined herein, and which is in the form of granules or a powder.

In further embodiments adhesive compositions, preferably medical or surgical glues, more preferably of adhesive compositions according to the invention comprising an adhesive-enhancing agent as defined herein has an adhesive shear strength (binding strength) between two supports expressed in Newton (N) as measured by the lap-shear testing method as described above which is at least 10%, and preferably at least 25%, or at least 50% or at least 75% higher than the adhesive strength measured in a same way for a similar composition lacking said adhesive-enhancing agent.

The adhesive-enhancing agent as defined herein can be added to the adhesive composition by any mixing method or mixing device well-known to a person skilled in the art including, such as but not limited to, hand-made mixing, mixing with an ultra-turax device or any other device suitable for obtaining a dispersion or a suspension of the granules within the adhesive composition.

Granules can be heterogeneously or homogeneously distributed within an adhesive composition. In some cases, a homogeneous distribution will be preferred whereas, in some other cases, a heterogeneous distribution will be preferred notably by creating a gradient of the granules concentration, or powder concentration enabling, for instance, a higher concentration of granules to be obtained close to outer surface of the adhesive composition which will be in contact with the tissue or the organ.

It is preferred to disperse or suspend the granules in such a way that they are well separated from each other within the adhesive composition. However, aggregation of the granules within the adhesive compositions is acceptable.

In particular embodiments the invention relates to adhesive compositions comprising
  chitin derivatives and/or chitin-glucan derivatives wherein
    said chitin derivatives and said chitin-glucan derivatives respectively are chitin polymers and chitin-glucan copolymers that are covalently coupled to polylactide;
a polar solvent, preferably water; and
optionally an adhesive-enhancing agent, wherein said adhesive-enhancing agent comprises granules of chitin or of chitin-glucan.

In particular embodiments the invention relates to adhesive compositions comprising
more than 5 wt %, and for instance more than 10 wt %, of chitin derivatives and/or chitin-glucan wherein said chitin derivatives and said chitin-glucan derivatives respectively are chitin polymers and chitin-glucan copolymers that are covalently coupled to polylactide;
more than 10 wt % and for instance more than 25 wt % of a polar solvent, preferably water; and
up to 60 wt %, and for instance between 1 and 35 wt % of an adhesive-enhancing agent; wherein said adhesive-enhancing agent comprises granules of chitin or of chitin-glucan, preferably an having average granule size which is lower than 1000 µm and for instance comprised between 10 and 250 µm.

In further particular embodiments the invention relates to adhesive compositions comprising
chitosan derivatives and/or chitosan-glucan derivatives wherein said chitosan derivatives and said chitosan-glucan derivatives respectively are chitosan polymers or chitosan-glucan copolymers that are covalently coupled to polylactide;
a polar solvent, preferably water; and
optionally an adhesive-enhancing agent, wherein said adhesive-enhancing agent comprise granules of chitin or of chitin-glucan.

In more particular embodiments the invention relates to adhesive compositions comprising
more than 5 wt %, and for instance more than 10 wt % of chitosan derivatives and/or chitosan-glucan derivatives wherein said chitosan derivatives and said chitosan-glucan derivatives respectively are chitosan polymers or chitosan-glucan copolymers that are covalently coupled to polylactide;
more than 10 wt % and for instance more than 25 wt % of a polar solvent, preferably water; and
up to 60 wt %, and for instance between 1 and 35 wt % of an adhesive-enhancing agent, wherein said adhesive-enhancing agent comprise granules of chitin or of chitin-glucan, preferably having an average granule size which is lower than 1000 µm and for instance comprised between 10 and 250 µm.

In an example, the invention provides an adhesive composition comprising:
more than 10 wt % of chitosan-glucan derivatives wherein said chitosan-glucan derivatives are chitosan-glucan copolymers that are covalently coupled to polylactic acid;
more than 10 wt % and for instance more than 25 wt % of a polar solvent, preferably water; and
up to 60 wt % and for instance between 1 and 35 wt % of an adhesive-enhancing agent, wherein said adhesive-enhancing agent comprise granules of chitin or of chitin-glucan having an average granule size which is lower than 1000 µm, and preferably comprised between 10 and 250 µm.

In another example, the invention provides an adhesive composition comprising:
more than 10 wt % of chitin-glucan derivatives wherein said chitin-glucan derivatives are chitin-glucan copolymers that are covalently coupled to polylactic acid;
more than 10 wt % and for instance more than 25 wt % of a polar solvent, preferably water; and
up to 60 wt %, and for instance between 1 and 35 wt % of an adhesive-enhancing agent, wherein said adhesive-enhancing agent comprise granules of chitin or of chitin-glucan having an average granule size which is lower than 1000 µm, and preferably comprised between 10 and 250 µm.

In particular embodiments the invention relates to adhesive compositions comprising
chitin derivatives and/or chitin-glucan derivatives wherein said chitin derivatives and said chitin-glucan derivatives respectively are chitin polymers and chitin-glucan copolymers that are covalently coupled to an amino-alkyl such as aminoethyl;
a polar solvent, preferably water; and
optionally an adhesive-enhancing agent, wherein said adhesive-enhancing agent comprises granules of chitin or of chitin-glucan.

In particular embodiments the invention relates to adhesive compositions comprising
more than 5 wt %, and for instance more than 10 wt % or more than 20 wt %, more than 30 wt %, more than 40 wt %, more than 50 wt %, more than 60 wt %, more than 70 wt %, more than 80 wt %, more than 90 wt %, and even up to 100 wt %, of chitin derivatives and/or chitin-glucan wherein said chitin derivatives and said chitin-glucan derivatives respectively are chitin polymers and chitin-glucan copolymers that are covalently coupled to an amino-alkyl such as amino-ethyl;
more than 10 wt % and for instance more than 25 wt % of a polar solvent, preferably water; and
up to 60 wt %, and for instance between 1 and 35 wt % of an adhesive-enhancing agent; wherein said adhesive-enhancing agent comprises granules of chitin or of chitin-glucan, preferably an having average granule size which is lower than 1000 µm and for instance comprised between 10 and 250 µm.

In further particular embodiments the invention relates to adhesive compositions comprising:
chitosan derivatives and/or chitosan-glucan derivatives wherein said chitosan derivatives and said chitosan-glucan derivatives respectively are chitosan polymers or chitosan-glucan copolymers that are covalently coupled to an amino-alkyl such as amino-ethyl;
a polar solvent, preferably water; and
optionally an adhesive-enhancing agent, wherein said adhesive-enhancing agent comprise granules of chitin or of chitin-glucan.

In more particular embodiments the invention relates to adhesive compositions comprising
more than 5 wt %, and for instance more than 10 wt % of chitosan derivatives and/or chitosan-glucan derivatives wherein said chitosan derivatives and said chitosan-glucan derivatives respectively are chitosan polymers or chitosan-glucan copolymers that are covalently coupled to an amino-alkyl such as amino-ethyl;
more than 10 wt % and for instance more than 25 wt % of a polar solvent, preferably water; and
up to 60 wt %, and for instance between 1 and 35 wt % of an adhesive-enhancing agent, wherein said adhesive-enhancing agent comprise granules of chitin or of chitin-glucan, preferably having an average granule size which is lower than 1000 µm and for instance comprised between 10 and 250 µm.

In particular embodiments adhesive compositions according to the invention further include one or more other biocompatible, preferably both biocompatible and bioresorbable materials. Said biocompatible materials may be either synthetic or natural polymers or mixtures of them. Biocompatible natural materials may for instance be selected from the group comprising proteins such as but not limited to collagen, gelatin, fibroin, fibrin, keratin, elastin, and casein and any combinations thereof; polysaccharides such as but not limited to glycosaminoglycans (such as e.g. hyaluronan, alginate, chondroïtine sulfate, heparine) pectin, pullulan, curdlan, cellulose, amidon, carraghenan, mannan, xylan, and dextran and any combinations thereof; and natural polyesters such as polymers selected from the group comprising polyhydroxyalcanoates, homo- and copolymers of hydroxybutyrate, hydroxyvalerate, polyorthoesters and polyurethanes and any combinations thereof.

Biocompatible synthetic polymers may for instance be selected from the group comprising biodegradable synthetic polyesters such as homopolymers and copolymers of lactic acid, glycolic acid, epsilon-caprolacton and p-dioxanone, and any other natural polyesters and any combination thereof.

In further particular embodiments, compositions according to the invention can also include pharmaceutically or biologically active compounds or drugs including but not limited to antimicrobial compounds, wound-healing drugs, growth factors, and any combinations thereof. Therefore the adhesive compositions may thus be used to deliver pharmaceutical or biological active compounds at the site of application.

An adhesive composition according to the invention can be provided or prepared in the form of a solution, gel, hydrogel, paste, foam, membrane, a stick, etc. thus in a form suitable for the application of the adhesive composition onto the site of application or administration; or in a form for suitable covering, coating, or impregnating a matrix. For instance, adhesive compositions according to the invention may be in the form of a paste, a liquid, a solution, a gel, a stick, a powder, a sponge, a foam, a membrane, a sheet or any other form well-known to a person skilled in the art. Said form may be suitable for being stored in a wet medium or can be stored in its dry form obtained notably by air-drying, freeze-drying or by any other drying method well known to a person skilled in the art.

Matrix

The present invention also provides a matrix that comprises an adhesive composition as described herein. The term "matrix" may include any type of material, device, surface, support, substrate, or the like, that can comprise an adhesive composition as defined herein. Such matrix can for instance be impregnated, covered, coated, spread by, dipped into, etc. with an adhesive composition as defined herein. The term "matrix" as used herein hence may in some embodiments be used as a synonym for "surface", "support" or "substrate". Matrices may include but are not limited to whether natural or synthetic surfaces or substrates such as a prosthesis, membrane, sheets woven or non-woven mesh, sponges for absorbing biological fluids, hemostatic sponges, bandages, yarns, staples and the like, which may be used to adhere to living tissues or organs both internally and externally.

In particular embodiments, the invention relates to the use of an adhesive composition as described herein above to treat a matrix. The term "treating a matrix" may include any type of treatment such as but not limited to coating, covering, impregnating a matrix.

Adhesive compositions according to the invention can be used to impregnate, cover, coat, spread on or around a support, such as a gels, woven or non-woven meshes, woven or non-woven polymeric supports, medical bandages, fibers, yarns, sutures, filaments, rods, surgical staples, membranes, sponges, foams, prosthesis, tubes, beads or any other valuable support such as implants aimed at being in contact with a tissue or an organ to which said support has to be fixed.

Adhesive compositions according to the invention are also suitable for covering, coating, impregnating, spreading onto any natural or synthetic surface or substrate, by any means well-known by the skilled person of the art such as dipping, rolling out or any other suitable tool, painting, spraying and the like, for the purpose of conferring adhesive properties to the surface or substrate to be stuck onto tissues or organs either internally or externally.

Adhesive compositions according to the invention or a support which is impregnated, coated or covered therewith can be removed from a surface without leaving any visible damage to the surface.

Adhesive compositions according to the invention or a support which is impregnated, coated or covered therewith can also be repositioned hence allowing a user, if needed, to remove, displace, reposition and fix by adhesion, either such adhesive compositions or support. Moreover, such repositioning can be performed in wet/humid environment. Thus Adhesive compositions according to the invention or a support which is impregnated, coated or covered therewith enable temporary and repeated fixation, said repeated fixation being possible in wet/humid environments which is not the case for commercial glues.

Method for the Preparation of Adhesive Compositions According to the Invention

A further aspect of the invention provides methods for preparing an adhesive composition according to the invention which comprises the steps of:

a) providing a composition comprising
   a suitable amount of a chitin and/or chitosan containing material as defined herein,
   optionally a suitable amount of one or more additional ingredients such as e.g. buffers, vehicles, additives, preservatives, excipients, adjuvants, plasticizers, fillers, anti-oxidants, or any other component that will render the composition suitable for a particular purpose, and
   optionally a suitable amount of an adhesive-enhancing agent as defined herein, and b) admixing a suitable amount of a polar solvent, preferably water to the composition obtained in step a).

Preferably the amounts of chitin and/or chitosan containing material, of solvent and or adhesive-enhancing agent are as defined above. The chitin and/or chitosan containing material, or the adhesive-enhancing agent can be applied in any of the forms as defined above. Mixing techniques applied in step b) are well known in the art and will not be discussed into detail herein.

Uses

In another aspect the invention relates to the use of an adhesive composition according to the invention or of a matrix comprising such adhesive composition. In particular the invention relates to the use of an adhesive composition comprising more than 10 wt % of a chitin and/or chitosan containing material provided in a polar solvent, preferably water, as a removable and repositionable adhesive.

More in particular the invention relates to the use of an adhesive composition comprising more than 10 wt % of a chitin and/or chitosan containing material provided in a polar solvent, preferably water, wherein no photochemical cross-linking is performed after application of the adhesive composition.

The adhesive compositions and matrices comprising them according to the present invention are characterized in that they can be used directly, i.e. adhere directly, without the need for photochemical cross-linking. This implies that the compositions can be used for direct adhesion, and methods of use do not involve irradiation or illumination.

In particular embodiments, the invention relates to an adhesive composition according to the invention or matrix comprising such composition for use as a medicament, and in particular for use as a surgical aid, and more in particular for use as a medical or surgical glue. The invention relates to the use of an adhesive composition or matrix according to the invention for the preparation of a medicament for gluing wounds, tissues, and organs.

The invention relates to a method of gluing wounds, tissues, and organs by administering to said wound tissue or organ an effective amount of an adhesive composition or of a matrix according to the invention.

The adhesive compositions and the matrices as defined herein may be used in many applications, e.g. in the field of surgical aids for improving the efficiency of classical sutures or for replacing them partially or totally and thus suppressing partially or totally the need of using yarns or staples or other invasive suture and tissue repair materials. They may also be used for fixing membranes, meshes, sheets, prosthesis, woven or non-woven polymers and yarns, medical bandages etc. . . onto living soft or hard tissues such as e.g muscles, skin, nerves, tendons, ligaments, blood vessels, bones, cartilages, nails, hair, teeth etc. . . that partially or totally suppress the need for using yarns, staples, screws, pins or other fixing devices that can damage or provoke additional injury to the tissue or nerves and provoke pain. The present adhesive compositions and the matrices as defined herein enable a perfect closure when needed and avoid leakage of fluids. Also the adhesive compositions and the matrices as defined herein enable to avoid excessive deformation of the tissue to be repaired.

Moreover, the adhesive compositions and the matrices as defined herein have beneficial effects in terms of wound healing, and may show haemostatic effects. The present adhesive compositions and the matrices as defined herein may also be used to prevent the formation of fibrin bits in wounds, and to prevent the formation of scars, and to support cell regeneration. Therefore, in particular embodiments, the invention relates to adhesive compositions or matrices according to the invention for use as a medicament, and in particular for use as a wound healing system. In further embodiments, the invention relates to adhesive compositions or matrices according to the invention for use as a medicament, and in particular for use as and/or haemostatic agent.

The invention also relates to an adhesive composition or matrix according to the invention for treating wounds, tissues or organs e.g. by adhering said composition or said matrix to said wounds, tissues or organs. In other words, the invention provides for the use of an adhesive composition or matrix according to the invention for the preparation of a medicament for treating wounds, tissues or organs, e.g. by adhering said composition or said matrix to said wounds, tissues or organs. More particularly the treatment involves adhering said composition or said matrix to said wounds, tissues or organs whereby the adhesive effect is inherent to the composition and thus no photo-irradiation is performed to ensure the adhesive effect. In yet further embodiments, the invention relates to a method for treating wounds, tissues or organs comprising the step of adhering an effective amount of an adhesive composition or matrix according to the invention to said wounds, tissues or organs of a subject in need thereof. More particularly, said methods are characterized in that they do not include the step of irradiating said composition after adhering said composition to said wounds, tissues or organs.

"Treating wounds" may include but is not limited to suturing, stitching, covering with a composition or matrix, closing openings or wounds, filling gaps, sticking or sealing two living tissues together, or sticking or sealing a living tissue to any other substrate such as an implantable material e.g. membranes, meshes, prostheses, yarns, staples, screws, pins and the like; preventing of the formation of scars, the formation of fibrin bits in wounds, improving of cell growth, inducing and/or increasing regeneration of cells and tissues etc.

The invention further relates to an adhesive composition or matrix according to the invention for removably or permanently fixing materials onto a tissue of a subject in need thereof. In other words, the invention provides for the use of an adhesive composition or matrix according to the invention for the preparation of a medicament for removably or permanently fixing materials onto a tissue of a subject in need thereof. In yet another embodiment, the invention relates to a method for removably or permanently fixing materials onto a tissue of a subject in need thereof comprising the step of applying a effective amount of an adhesive composition or matrix according to the invention to a subject in need thereof.

The term "effective amount" in the present context refers to that amount of active compound(s) that activate(s) the biological or medical response in a tissue, system, animal or man, which is intended by a researcher, surgeon, veterinary surgeon, dentist or doctor, and which contains reducing the symptoms of that disease or disease that is treated. The effective amount depends on the disease to treat and the professional skills of the therapist.

In particular embodiments, the invention relates to the use of an adhesive-enhancing agent as defined above in an adhesive composition. An adhesive-enhancing agent as defined above can be used in any type of gluing composition, and preferably in any type of medical or surgical glue.

In a preferred embodiment, the invention relates to the use of an adhesive-enhancing agent as defined above in an adhesive composition as defined herein.

In particular embodiments, the invention relates to adhesive-enhancing agents as described herein above as adhesive enhancers. The invention relates to the use of an adhesive-enhancing agent as described above for improving adhesiveness of an adhesive composition which can be any type of gluing composition, and more preferably of an adhesive composition as defined herein. The invention therefore also relates to a method for improving the adhesiveness of an adhesive composition which can be any type of gluing composition, and more preferably of an adhesive composition as defined herein, by adding an adhesive-enhancing agent as described herein to said adhesive composition. In further particular embodiments, the invention relates to an adhesive-enhancing agent as defined above as adhesion accelerator. The invention hence also relates to the use of an adhesive-enhancing agent as defined above for accelerating adhesion to a matrix or to a wound, tissue, or organ tissue, organ of an adhesive composition of an adhesive composition which can be any type of gluing composition suitable for that purpose, and more preferably of an adhesive composition as defined herein. Similar to the adhesive compositions described hereinabove, the adhesive compositions comprising an adhesive enhancing agent are adhesive per se and do not require photo-irradiation. Methods of use of these compositions do not comprise the step of photo-irradiating the composition after it has been applied. The invention therefore also relates to a method for accelerating adhesion to a matrix or to a wound, tissue, or organ tissue, organ of an adhesive composition which can be any type of gluing composition, and more preferably of an adhesive composition as defined herein.

The invention will now be illustrated with the following non-limiting examples.

EXAMPLES

Example 1

Preparation of Adhesive Compositions According to the Invention

Chitosan-glucan and chitin-glucan copolymers based derivatives were synthesized according to methods known in the prior art. Chitosan-glucan and chitin-glucan copolymers used for preparing said derivatives were obtained from a fungal source (*Aspergillus niger* or *Agaricus bisporus*) according to methods such as those described in WO03068824; which is incorporated herein by reference. Adhesive compositions comprising these derivatives where subsequently prepared to form of a paste.

1.1. Preparation of Chitosan, Chitin or Chitin-glucan Based Derivatives—Synthesis Amino-ethyl chitin and amino-ethyl chitin-glucan have been synthesized according to Jae-Young et al. (Jae-Young et al., Biochimica et Biophysica Acta, 1760 (2006) 104-109). Typically, 3 g of chitin or chitin-glucan copolymers both obtained from *Aspergillus niger* were added to 150 ml of a 3M aqueous solution of 2-chloroethylamino hydrochloride. This suspension was magnetically stirred and heated at 65° C. 75 ml of 6M NaOH solution was added drop by drop to this suspension and the stirring was maintained 24 h. After reaction, unreacted chitin (or chitin-glucan) was removed by filtration. Subsequently, the reaction mixture was acidified until reaching pH=5 by addition of HCl 0.1M. The final product was purified by dialysis (cut-off=3500 g/mol) against water during 3 days. The final derivative was recovered by freeze-drying before being characterized (Table 1).

TABLE 1

Structural characteristics of amino-ethyl chitin-glucan and amino-ethyl chitin-glucan prepared in Example 1

| Sample | Derivative type | Molar ratio between chitin and glucan | Mass ratio between reagents[a] |
|---|---|---|---|
| AECG2 | Amino-ethyl chitin-glucan | 71/29 | 16.6 |
| AECG1 | Amino-ethyl chitin-glucan | 28/72 | 17.4 |

[a]mass ratio between 2-chloroethylamino hydrochloride and chitin (or chitin-glucan) used for the synthesis Chitosan-glucan copolymer obtained from deacetylation of chitin-glucan from *Agaricus bisporus* has been trimethylated according to the published two steps method of Sieval et al. (Sieval et al., Carbohydrate Polymers, 36 (1998) 157-165). Chitosan polymer (10.85 g) was dissolved in NMP (400 mL) with sodium iodide (24 g) at 60° C. under stirring in a round bottom flask. After 30 minutes, sufficient NaOH (56 mL of 15% NaOH) was added in order to maintain an alkaline environment throughout the reaction. The methylation was achieved 30 minutes later through nucleophilic substitution by addition of methyl iodide (53 mL) to the solution. The reaction was maintained during 90 minutes at 60° C. under reflux conditions. The solution was collected and filtered through glass sinter filters (Pyrex 2) and the supernatant was collected. Products were precipitated then by addition of 1 L of diethyl ether:ethanol (1:9 v/v) and washed twice thoroughly with ethanol and ether. After drying in vacuum one night, the product was again dissolved in 400 mL NMP and 52 mL of 15% w/v NaOH was added to the solution. After 30 minutes, 35.3 mL of methyl iodide was added and the reaction was left under reflux for 30 minutes. Next, 2 g NaOH pellets and 23.5 mL MeI were added and reaction continued for further 60 min. The final solution was filtered through glass sinter filters (Pyrex 2) and the supernatant was collected. Products were then precipitated then by addition of 1 L of diethyl ether:ethanol (1:9 v/v) and washed twice with ethanol and diethyl ether. After drying in vacuum overnight, the finalized product was dissolved in 200 mL of 0.5M NaCl solution to replace the counter-ion and to prevent iodine oxidation. Following precipitation with 500 mL of diethyl ether:ethanol (1:9 v/v), the product was washed twice with ethanol and diethyl ether and again dissolved in 200 mL MQ water. The solution was finally purified by dialysis (cut-off=3500 g/mol) against water for 3 days and the final product was by freeze-dried before characterization (Table 2).

TABLE 2

Structural characteristics of the trimethyl chitosan-glucan prepared in Example 1

| Sample | Derivative type | Chitosan-Glucan Mw(DA) | Degree of trimethylation[a] | Degree of dimethylation[a] |
|---|---|---|---|---|
| TMC | Trimethyl chitosan-glucan | 42000 | 60% | 29% |

[a]molar ratio

Chitosan-glucan copolymer grafted with polylactic acid was prepared by polycondensation of lactic acid on chitosan according to Yao et al. (Polymer, 44 (2003) 6435-6441). Typically, 2 g of chitosan-glucan obtained from deacetylation of chitin-glucan from *Agaricus bisporus* are dissolved in 40 mL of lactic acid syrup (10% of residual water) at 65° C. over night. The residual water was removed by evaporation from this solution at 65° C. under vacuum for 30 minutes. The polycondensation reaction was initiated by increasing the temperature and the vacuum to at least 90° C. and 2 mBar, respectively. The reaction was maintained during at least 150 minutes under these conditions (Table 3a). Afterwards the product was precipitated by addition of 400 mL of acetone and washed twice thoroughly using fresh portions of acetone. After drying in vacuum overnight, the finalized product was dissolved in 100 mL of water. Minute amounts of a 0.2M NaOH solution was added drop by drop to this solution in order to reach a neutral pH value. The solution was finally purified by dialysis (cut-off=3500 g/mol) against water for 3 days and the final product was recovered by freeze-dried before characterization (Table 3b).0

TABLE 3a experimental parameters for preparing chitosan-glucan-PLA polymers of Example 1

| Sample | Chitosan-glucan Mw (DA) | Amount of CsG | Volume of lactic acid | Reaction T°(C.°) | Reaction time (h) |
|---|---|---|---|---|---|
| CsG-PLA1 | 50 | 2 | 40 | 110 | 7 |
| CsG-PLA2 | 50 | 2 | 40 | 90 | 21 |
| CsG-PLA3 | 100 | 2 | 40 | 90 | 7 |
| CsG-PLA4 | 25 | 2 | 15 | 90 | 7 |
| CsG-PLA5 | 50 | 2 | 40 | 90 | 7 |

TABLE 3a-continued experimental parameters for preparing
chitosan-glucan-PLA polymers of Example 1

| Sample | Chitosan-glucan Mw (DA) | Amount of CsG | Volume of lactic acid | Reaction T°(C.°) | Reaction time (h) |
|---|---|---|---|---|---|
| CsG-PLA6 | 50 | 2 | 40 | 90 | 7 |
| CsG-PLA7 | 77 | 4 | 80 | 100 | 7 |

TABLE 3b

Structural characteristics and surface-activity of
chitosan-glucan-PLA polymers prepared in Example 1

| Sample | Chitosan-glucan Mw (DA) | Degree of substitution $(DS)^a$ | Degree of polymerization $(DP)^b$ | LA/Cs monomer ratio$^c$ | Surface tension (mN/m) |
|---|---|---|---|---|---|
| CsG-PLA1 | 50 | 0.59 | 7 | 4.1 | 48.8 |
| CsG-PLA2 | 50 | 0.44 | 7 | 3.1 | 52.3 |
| CsG-PLA3 | 100 | 0.16 | 10 | 1.6 | 64.9 |
| CsG-PLA4 | 25 | 0.25 | 6 | 1.5 | 62.7 |
| CsG-PLA5 | 50 | 0.1 | 10 | 1 | 62.3 |
| CsG-PLA6 | 50 | 0.2 | 6 | 1.2 | 62.7 |

$^a$molar ratio
$^b$average number of lactic repeating units on one PLA chain grafted
$^c$DP × DS Octanoyl chitin-glucan has been synthesized according to Pifferi (Pifferi et al., Italian Journal of Food Science, 2 (2001) 173-188). 2.21 g of chitin-glucan (from *Aspergillus niger*) was added to 15 ml of methansulfonic acid under stirring at 5° C. After a few minutes, a gel was formed, to which 11.7 ml of octanoyl chloride were added. The mixture was stirred for 5 h at 5° C., and the temperature was then lowered to −20° C. for about 18 h. The product, precipitated by adding 200 mL of cold water (3°-4° C.), was washed once with 200 mL of cold water and once with 200 mL of cold water containing 5 ml of NH$_3$ 25%. The solid, washed thoroughly with distilled water was dried under vacuum at 40° C. and then suspended in diethyl ether. A series of washes were then performed, first with diethyl ether and then with ethanol. The final product was left to dry under vacuum at 40° C. overnight.

TABLE 4

Structural characteristics of Octanoyl
chitin-glucan prepared in Example 1

| Sample | Derivative type | Molar ratio between chitin and glucan | Mass ratio between reagents$^a$ |
|---|---|---|---|
| OCG | Octanoyl chitin-glucan | 34/66 | 5 |

$^a$mass ratio between octanoyl chloride and chitin-glucan used for the synthesis 1.2. Preparation of the Adhesive Compositions 3 g of the chitosan-glucan, chitin or chitin-glucan derivatives prepared in this Example (paragraph 1.1) were added to 10 ml of water. The resulting 23 wt % (it is % by weight or w/w) paste was vigorously mixed at room temperature until visible homogeneity. If necessary, pH can be adjusted to 7 using NaOH 0.2M. The resulting adhesive compositions were in the form of pastes.

Example 2

Adhesive Characteristics of Adhesive Compositions on Different Substrates

The adhesiveness of different adhesive compositions as prepared in Example 1, were tested on different surfaces, i.e. glass, ham and porcine skin tissue.

Prior to their use, the samples of ham and porcine skin tissue were rinsed with a phosphate buffer solution at pH 7.2.

The lap-shear testing method described by the procedure edited in ASTM F2255-03 "Standard test method for strength properties of tissues adhesives in lap-shear by tension loading" was used. In this test, two supports are glued together using a glue or adhesive composition to be tested and the adhesive shear strength to disrupt the adhesive joint is then determined as the maximum force (expressed in Newton (N)) needed to separate the two supports.

Thus, in this Example 2, supports glued together were either two pieces of glass or two pieces of ham or two pieces of porcine skin tissue, the ham and porcine skin being strongly fixed to a solid glass support by means of cyanoacrylate glue.

About 200 mg of the tested adhesive compositions were spread on 5 cm$^2$ of one of the two pieces of glass, ham or porcine skin tissue, the other piece being left untreated. The two pieces (one treated and the other untreated) of glass, ham or porcine skin were then overlapped together and put in a mechanical press at 37° C. No pressure was applied and the mechanical press was only intended to keep the supports in contact during 5 or 15 minutes.

After this contact time (or conditioning time), the glued supports were attached to the tension fixature of a mechanical analyser instrument (Instron R, model 5566). The upper fixature was separated from the lower one at a constant rate of 5 mm/minute until the adhesive joint disrupted. The adhesive shear strength was determined as the maximum force (expressed in Newton (N)) for separation of the two supports to occur.

Experiments were performed with the adhesive compositions prepared in Example 1. They were compared to commercial glues, e.g. to fibrin glue (Tissucol, Baxter), polyurethane glue (UHU Extra gel, UHU) and/or to epoxyde glue (Kombi rapide, Bison). Comparative results are given in FIG. 1a (glass), FIG. 1b (ham) and FIG. 1c (porcine skin tissue).

Example 3

Adhesiveness and Repositionability of Adhesive Compositions Comprising CsG-PLA—Adhesion and Repositioning at the Same Site of Application Chitosan-PLA derivatives CsG-PLA1, CsG-PLA2 and CsG-PLA3 of Example 1 (table 3) were used to prepare adhesive compositions according to the method described in paragraph 1.2 of Example 1. Both adhesion and repositionability of these adhesive compositions were tested on ham using the lap-shear testing method described in Example 2. Fibrin glue (Tissucol) was used as a control.

In a first step, adhesiveness was tested after 5 and 15 minutes contact time (mechanical press, room temperature, no pressure). Results are given in FIG. 2 and FIG. 3 left bar for each tested sample. After disruption, in a second step, the two separated pieces were overlapped together again during a contact time of 5 and 15 minutes and the force needed to separate them again was measured FIG. 2 and FIG. 3 (right bar for each tested sample).

Figure 2:
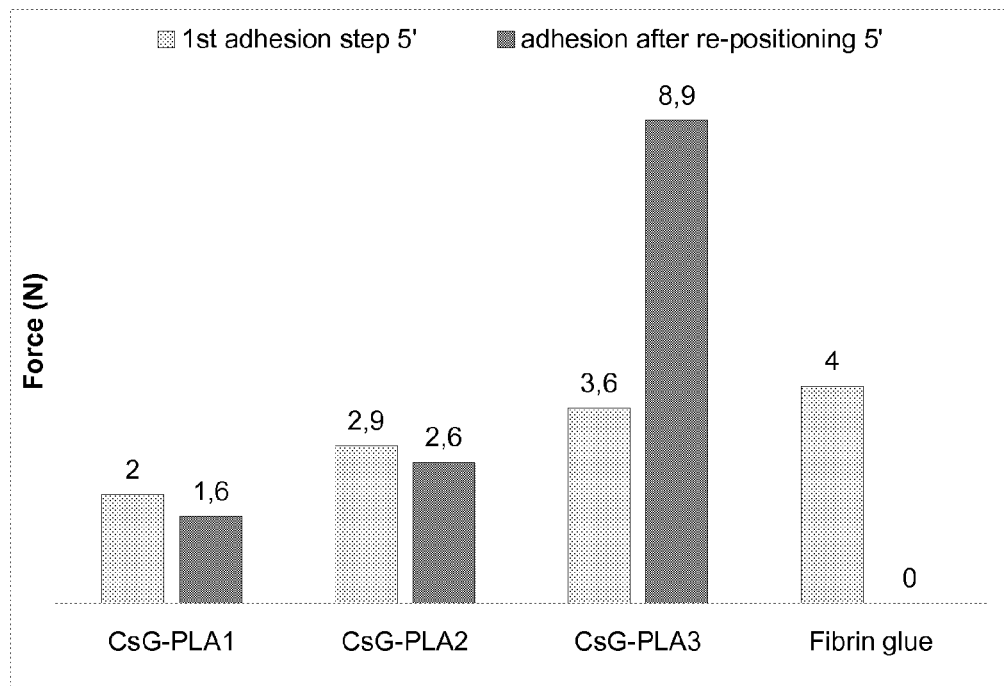
FIG. 2 shows the adhesiveness of embodiments of adhesive compositions according to the invention containing CsG-PLA polymers compared to fibrin glue on a ham substrate. Removability and re-positionability of said compositions compared to fibrin glue after 5 minutes of adhesion is illustrated.
Figure 3:
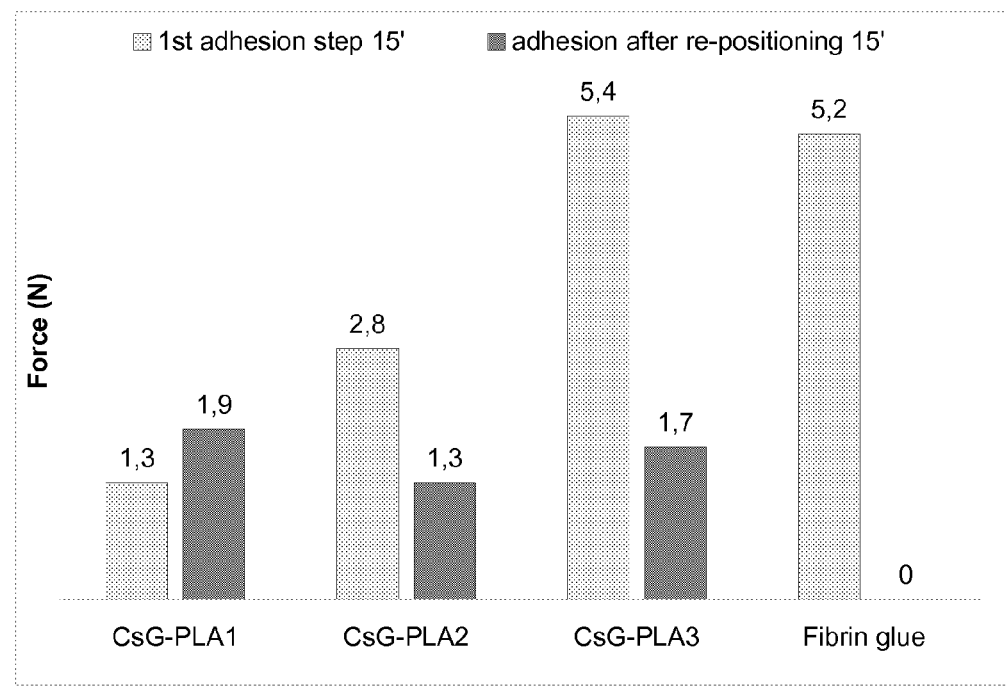
FIG. 3 shows the adhesiveness of embodiments of adhesive compositions according to the invention containing CsG-PLA polymers compared to fibrin glue on a ham substrate. Removability and re-positionability of said compositions is compared to fibrin glue after 15 minutes of adhesion.

The results of FIG. 2 and FIG. 3 (left bar for each tested samples) show a good adhesion of compositions comprising CsG-PLA1, CsG-PLA2 and CsG-PLA3, comparable to fibrin glue irrespective the time used before testing (5 and 15 minutes). The results of FIG. 2 and FIG. 3 (right bar for each tested sample) illustrate that the fibrin glue does not allow a repositioning followed by adhesion. On the contrary, compositions comprising CsG-PLA samples were able, after a first adhesion step, to be re-positioned and to further adhere once again without losing adhesiveness irrespective the time used before testing (5 and 15 minutes).

Example 4

Adhesiveness of Adhesive Compositions Comprising Chitin-glucan Micrgranules—Adhesion and Re-positioning at the Same Site of Application Chitosan-PLA derivative CsG-PLA4 of Examples 1 was used to prepare an adhesive composition according to the method disclosed in paragraph 1.2 of the Example 1. Then 30% (w/w) of chitin-glucan microgranules having an average granule size ranging from 30 to 125 µm were added to the paste. The system was vigorously mixed at room temperature until visible homogeneity. The same method for testing the adhesiveness and repositionability as explained in Example 3 was used, but in this Example 4 porcine skin tissue was used instead of ham. The contact time (mechanical press, room temperature, no pressure) was 15 minutes.

Figure 4A:
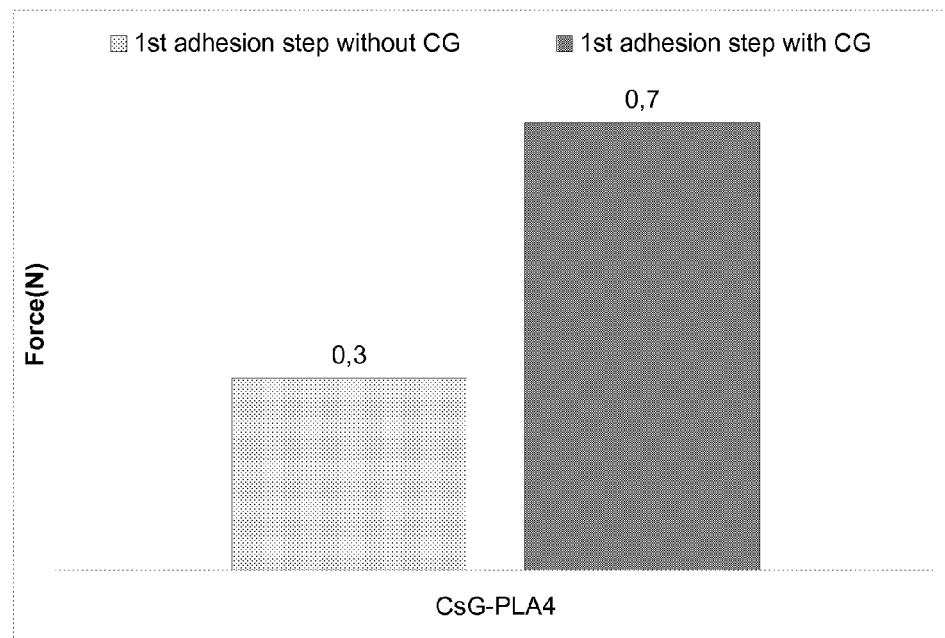
FIGS. 4a and 4b illustrate adhesiveness and repositionability of embodiments of adhesive compositions according to the invention containing CsG-PLA polymers with and without chitin-glucan granules on a porcine skin tissue.
Figure 4B:
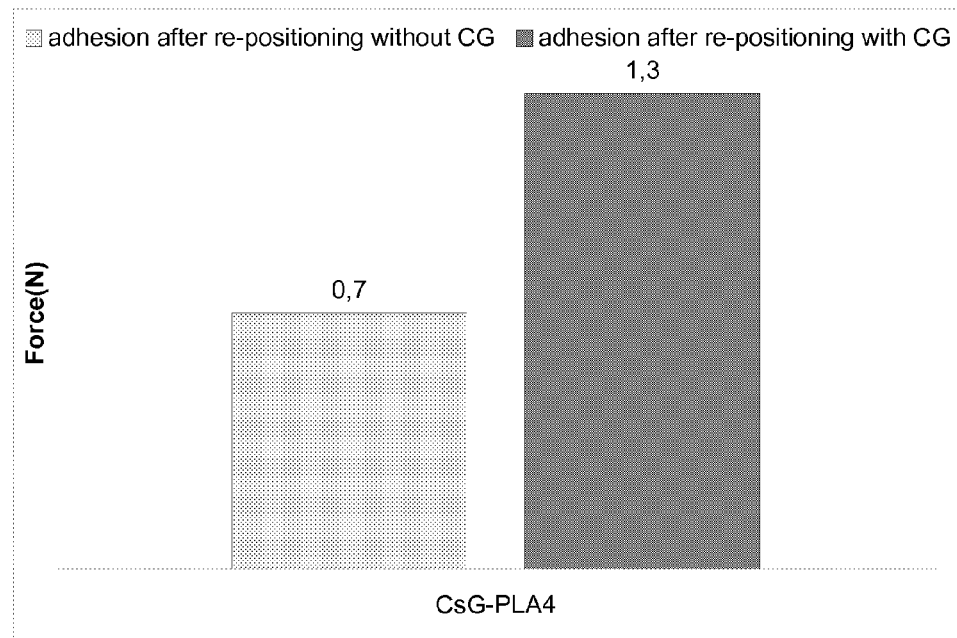

The adhesive shear strength values measured after the first adhesion step are shown in FIG. 4a for the adhesive compositions comprising CsG-PLA4 with and without added microgranules of chitin-glucan. The adhesive shear strength values measured after re-positioning and adhesion of the compositions at the same site of adhesion are shown in FIG. 4b.

The results obtained in this Example 4 demonstrate that the chitin-glucan granules added to an adhesive composition enable to enhance the adhesive strength to a tissue. The chitin-glucan granules act as an adhesion enhancer. Moreover the presence of chitin-glucan micro-granules allows removal and re-positioning of the adhesive composition with an adhesion strength which can be equal or even higher than the adhesive strength measured during the first adhesion step (more than 80% increase).

Example 5

Adhesiveness and Repositionability of Adhesive Compositions Comprising CsG-PLA5 and CsG-PLA6—Adhesion and Re-positioning on Two Different Sites of Application Chitosan-PLA derivatives CsG-PLA5 and CsG-PLA6 were used to prepare adhesive compositions according to the method of Example 1, paragraph 1.2. Similarly to Example 4, 30% (w/w) of chitin-glucan micro-granules (average granule size ranging from 30 to 125 µm) were added to the paste and mixed until visible homogeneity.

The same experiment was performed as in Example 4 but, instead of performing the re-positioning and second adhesion at the same site of application, this time, both were performed elsewhere on another portion of the porcine skin tissue.

Figure 5:
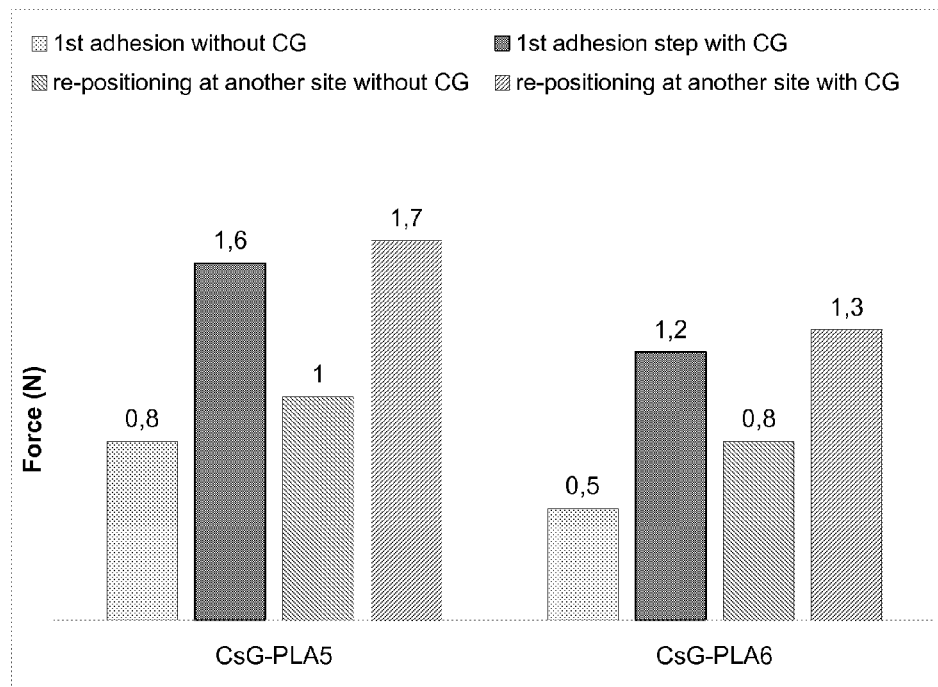
FIG. 5 illustrates adhesiveness on a first site on porcine skin tissue of embodiments of adhesive compositions according to the invention containing CsG-PLA polymers with and without chitin-glucan granules and repositionability on a second site on porcine skin tissue of said embodiments of adhesive compositions. The first site of adhesion and the second site of adhesion after repositioning are different.

FIG. 5 shows:
a) On the four lefts bars, the adhesion of compositions comprising CsG-PLA5 and CsG-PLA5+Chitin-glucan microgranules during the first adhesion step (2 first bars) and after re-positioning/adhesion at another site of adhesion (2 last bars)
b) On the four right bars, the adhesion of compositions comprising CsG-PLA6 and CsG-PLA6+Chitin-glucan microgranules during the first adhesion step (2 left bars) and after re-positioning/adhesion at another site of adhesion (2 last bars)

The results confirm an adhesion enhancement effect of chitin-glucan micro-granules and show the repositioning ability of adhesion compositions comprising CsG-PLA with and without chitin-glucan micro-granules when fixed on another site of application.

Example 6

Adhesiveness of Medical Bandage Coated/Impregnated with an Adhesive Composition with Chitin-glucan Micro-granules Chitosan-derivative CsG-PLA6 was used to prepare an adhesive composition according to the method of paragraph 1.2, example 1. Similarly to Examples 4 and 5, 30% (w/w) of chitin-glucan micro-granules (30-125 µm) were mixed into the paste until visible homogeneity. A 20 $cm^2$ surface of a medical bandage (Cambric bandages, Holthaus medical) was covered and partially impregnated by the composition comprising CsG-PLA6 polymers and chitin-glucan granules.

Figure 6:
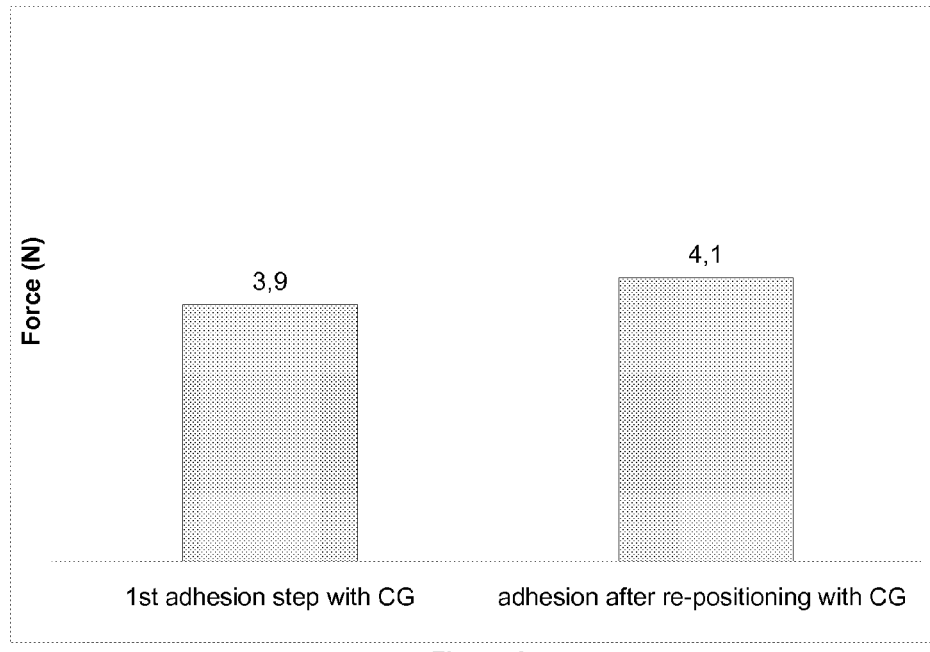
FIG. 6 illustrates adhesiveness and re-positionability of a medical bandage coated with an adhesive compositions containing CsG-PLA polymers and chitin-glucan granules on porcine skin tissue.

Adhesion of the coated/impregnated bandage was tested on porcine skin tissue according to the test method of Example 5, thus including a first adhesion step of the bandage, followed by its removal, re-positioning and adhesion on another site of the porcine skin. Results are shown on FIG. 6. The bandage covered/impregnated by the adhesive composition is able to adhere, to be removed and to adhere once again at another site of application without losing adhesiveness.

Example 7

Use of the Adhesive Composition in vivo (Rats)

An adhesive composition used for experiments here below is a sample of CsG-PLA. This sample was prepared according to the same experimental conditions as those described in table 3a for sample no CsG-PLA1. The sample has been sterilized by gamma irradiation prior to use.

7.1. Use of an Adhesive Composition According to the Invention in vivo on Rats after Oesophageal Section After anesthesia of the animals Fisher rats male and female, a section of the cervical esophagus is performed and sutured using Prolene 7/0. The suture is dried using a gaze or a cotton stalk and the suture points are reinforced by application of an adhesive composition according to the invention on the suture line. The adhesive composition is spread using a metallic spatula, in a thin film of 1-mm thickness as homogenously as possible. The adhesive composition is applied at room temperature. After one minute, we can observe the presence of a thin, supple and transparent film where the adhesive composition was spread; the wound is rapidly closed. Histological observations show the presence of residual adhesive composition at the sutured site. Thus the composition as disclosed in this example allows to reinforce sutures, and to decrease the number of suture points.

7.2 Use of an Adhesive Composition According to the Invention for Suturing Skin

On rats, a skin section of 1 to 3 cm length was performed using a scalpel or scissors at the neck, abdomen or back level.

The section was sutured (distance between points varying from 5 to 10 mm) and an adhesive composition according to the invention was spread (with a spatula, layer of 1 mm thick), at room temperature, on the edges of the section after adaptation of the edges of the wound and drying. Arylic resin was used as control (adhesive for external use which solidifies and forms a crust that detaches after a few days). Criteria such as the dehiscence of the wound edges, the evolution of the redness of the edges, the swelling, histology, wound healing when using the composition of the present invention were compared both to those observed when other commercial adhesive composition and without any adhesive composition.

The composition according to the invention did not form any crust, avoided the edges of the wound to separate. It enabled to increase the distance between suture points (10 mm instead of 5 mm) which evidenced that an adhesive compositions of the present invention may strengthen sutures.

Example 8

Preparation of Chitosan Based Derivatives 8.1 Synthesis of Aminoethyl Chitosan (AE-Cs)

Aminoethyl chitosan compounds have been synthesized according to Jae-Young et al. (Jae-Young et al., Biochimica et Biophysica Acta, 1760 (2006) 104-109). Typically, 10 g of chitosan obtained from *Agaricus bisporus* (KitoZyme, batch number L09125CsU) was added to 500 ml of an aqueous solution of 2-chloroethylamino hydrochloride (variable concentration depending on the desired molar ratio between chitosan and the reagent). This suspension was magnetically stirred and heated at 65° C. 250 ml of 6M NaOH solution was added drop by drop to this suspension and the stirring was maintained for 24 h. After reaction, the unreacted chitosan was removed by filtration. Subsequently, the reaction mixture was acidified until pH=5 with HCl 0.1M. The final product was purified by dialysis (cut-off=3500 g/mol) against water during 3 days. The final derivative was recovered by freeze-drying and characterized (Table 5).

TABLE 5

Structural characteristics of aminoethyl chitosan (AE-Cs)

| Sample | Derivative type | Molar ratio between chitin and 2-chloroethyl-aminohydrochloride | Concentration of the reagent solution |
|---|---|---|---|
| AECs1 | Aminoethyl chitosan | 1/5 | 0.6 mol/l |
| AECs2 | Aminoethyl chitosan | 1/15 | 1.8 mol/l |
| AECs3 | Aminoethyl chitosan | 1/25 | 3 mol/l |

8.2 Preparation of the Adhesive Compositions 3 g of the aminoethyl chitosan (AE-Cs) derivatives prepared according to the above was added to 10 ml of water. The resulting 23 wt % (m/v) paste was vigorously mixed at room temperature until visible homogeneity. Optionally, pH can be adjusted at 7 using NaOH 0.2M. The resulting adhesive compositions were in the form of pastes.

Example 9

Adhesiveness and Repositionability of Adhesive Compositions Comprising AE-Cs—Adhesion and Repositioning at the Same Site of Application AE-Cs derivatives AECs1, AECs2 and AECs3 according to Example 8 were used to prepare adhesive compositions according to the method described in paragraph 8.2 of Example 8. Both adhesion and repositionability of these adhesive compositions were tested on porcine skin tissue using the lap-shear testing.

The adhesiveness of the adhesive compositions was tested on porcine skin tissue. Prior to their use, the samples of porcine skin tissue were rinsed with a phosphate buffer solution at pH 7.2.

The lap-shear testing method described by the procedure edited in ASTM F2255-03 "Standard test method for strength properties of tissues adhesives in lap-shear by tension loading" was used. In this test, two supports are glued together using a glue or adhesive composition to be tested and the adhesive shear strength to disrupt the adhesive joint is then determined as the maximum force (expressed in Newton (N)) needed to separate the two supports.

Thus, in this example, supports glued together were two pieces of porcine skin tissue, the porcine skin being strongly fixed to a solid glass support by means of cyanoacrylate glue. About 200 mg of the tested adhesive compositions were spread on 5 cm$^2$ of one of the two pieces of porcine skin tissue, the other piece being left untreated. The two pieces (one treated and the other untreated) of porcine skin were then overlapped together and put in a mechanical press at 37° C. No pressure was applied and the mechanical press was only intended to keep the supports in contact during 5 minutes.

After this contact time, the glued supports were attached to the tension fixture of a mechanical analyser instrument (Instron R, model 5566). The upper fixture was separated from the lower one at a constant rate of 5 mm/minute until the adhesive joint disrupted. The adhesive shear strength was determined as the maximum force (expressed in Newton (N)) for separation of the two supports to occur. Experiments were performed with the adhesive compositions prepared from AECs in Example 8.

Figure 7:
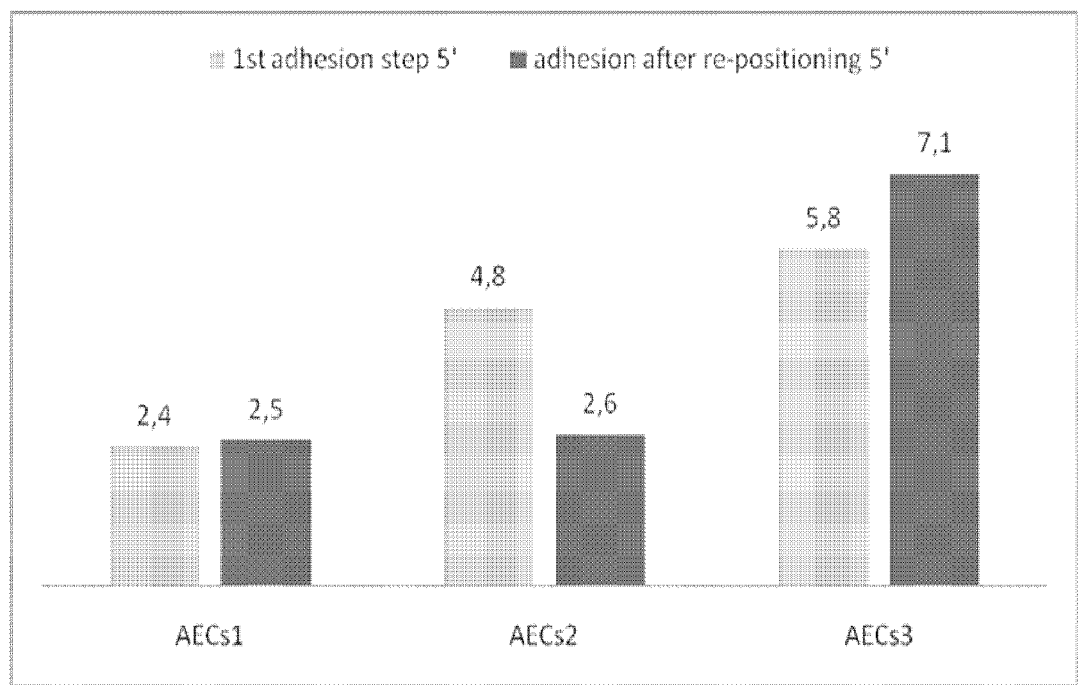
FIG. 7 illustrates adhesiveness and re-positionability of embodiments of adhesive compositions according to the invention containing aminoethyl-chitosan (AE-Cs) polymers on a porcine skin substrate.

In a first step, adhesiveness was tested after 5 minutes contact time (FIG. 7 left bar for each tested sample). After disruption, in a second step, the two separated pieces were overlapped together again during a contact time of 5 minutes and the force needed to separate them again was measured (FIG. 7 right bar for each tested sample).

The results shown in FIG. 7 show a good adhesion after 5 minutes (left bar for each tested sample) of compositions comprising AECs1, AECs2 and AECs3. The adhesive strength for the first adhesion increases with the amount of reagent used to prepare the derivative. AECs1 was prepared with the lowest molar ratio between chitosan and 2-chloroethylamino hydrochloride (see table 5). The adhesive strength for this sample is 2.4N. AECs3 was prepared with the highest molar ratio between chitosan and 2-chloroethylamino hydrochloride. The adhesive strength for this sample is 5.8N. The higher the amount of reagent used, the higher the adhesive strength of the adhesive formulation. The results of FIG. 7 (right bar for each tested sample) also illustrate that the AE-Cs glues were able, after a first adhesion step, to be re-positioned and to further adhere once again.

What is claimed is:

1. An adhesive composition wherein said composition is removable and repositionable and comprises more than 10 wt % of a chitin and/or chitosan containing material provided in a polar solvent, preferably water, wherein said chitin and/or chitosan containing material are not photochemically cross-linked; and wherein said chitin and/or chitosan containing material is selected from chitin derivatives, chitin-glucan, chitosan derivatives, chitosan-glucan or derivatives thereof, and any combinations thereof, wherein said chitosan derivatives comprise glucosamine monomers and N-acetyl glucosamine monomers.

2. The adhesive composition according to claim 1 wherein said composition has an adhesive shear strength between two supports of at least 0.1 Newton (N) as measured by a lap-shear testing method based on ASTM F2255-03.

3. The adhesive composition according to claim 1, wherein said composition comprises more than 10 wt % of water.

4. The adhesive composition according to claim 1, wherein said chitosan derivatives or said chitosan-glucan derivatives respectively are chitosan polymers or chitosan-glucan copolymers that are covalently coupled to aliphatic polyesters, and preferably to polylactic acid (PLA).

5. The adhesive composition according to claim 4, wherein said polylactic acid has a degree of polymerization which is lower than 1000.

6. The adhesive composition according to claim 1, wherein said chitin, chitin-glucan, chitosan derivatives or chitosan-glucan derivatives are polymers covalently coupled to an amino-alkyl such as amino-ethyl (AE).

7. The adhesive composition according to claim 1, wherein said chitosan polymers are coupled to polylactic acid and consist of polymers comprising N-acetyl-glucosamine monomers, glucosamine monomers, and lactic acid monomers, wherein the ratio of (I) total number of lactic acid monomers to (II) total number of N-acetyl-glucosamine monomers and glucosamine monomers is comprised between 0.1 and 1000; and wherein said chitosan-glucan copolymers coupled to polylactic acid consist of polymers comprising N-acetyl-glucosamine monomers, glucosamine monomers, glucose monomers, and lactic acid monomers, wherein the ratio of (I) total number of lactic acid monomers to (II) total number of N-acetyl-glucosamine monomers and glucosamine monomers and glucose monomers is comprised between 0.1 and 1000.

8. The adhesive composition according to claim 1, further comprising at least one adhesive-enhancing agent, wherein said agent is provided in the form of granules.

9. The adhesive composition according to claim 8, wherein said adhesive-enhancing agent is provided in the form of granules having an average granule size which is lower than 1000 μm.

10. The adhesive composition according to claim 8, wherein adhesive-enhancing agent is present in said composition in an amount of up to 60 wt %.

11. The adhesive composition according to claim 8, wherein said adhesive-enhancing agent comprises a chitin and/or a chitosan containing material.

12. The adhesive composition according to claim 11, wherein said adhesive-enhancing agent consists of granules of chitin and/or of chitin-glucan.

13. The adhesive composition according to claim 1 comprising
more than 10 wt % of chitosan-glucan derivatives wherein said chitosan-glucan derivatives are chitosan polymers that are covalently coupled to a functional group such as polylactic acid or an amino-alkyl such as amino-ethyl,
more than 10 wt % of a polar solvent, preferably water; and
up to 60 wt % of an adhesive-enhancing agent, wherein said adhesive-enhancing agent comprises granules of chitin or of chitin-glucan having an average granule size which is lower than 1000 μm.

14. A matrix comprising an adhesive composition as defined in claim 1.

15. A method for gluing wounds, tissues, and organs said method comprising administering to said wound tissue or organ an effective amount of a matrix according to claim 14.

16. A method for fixing a membrane, mesh, sheet, woven or non-woven polymers and yarns, medical bandages onto living soft or hard tissues comprising applying an effective amount of an adhesive composition according to claim 1 onto said membrane, mesh, sheet, woven or non-woven polymers and yarns, medical bandages or onto said living soft or hard tissues.

17. A method for treating a wound comprising the step of covering said wound with an effective amount of an adhesive composition which is removable and repositionable according to claim 1 or a matrix comprising said adhesive composition.

18. The method according to claim 17 characterized in that it does not include the step of irradiating said composition after adhering said composition to said wound.

* * * * *